(12) United States Patent
Murakami et al.

(10) Patent No.: US 10,525,471 B2
(45) Date of Patent: Jan. 7, 2020

(54) TARGET ANALYSIS CHIP AND TARGET ANALYSIS METHOD

(71) Applicants: ARKRAY, Inc., Kyoto (JP); NATIONAL UNIVERSITY CORPORATION KYOTO INSTITUTE OF TECHNOLOGY, Kyoto (JP)

(72) Inventors: Akira Murakami, Kyoto (JP); Akio Kobori, Kyoto (JP); Asako Yamayoshi, Kyoto (JP); Yuichiro Noda, Kyoto (JP); Masayuki Kondo, Kyoto (JP)

(73) Assignees: ARKRAY, Inc., Kyoto (JP); National University Corporation Kyoto Institute of Technology, Kyoto (JP)

( * ) Notice: Subject to any disclaimer, the term of this patent is extended or adjusted under 35 U.S.C. 154(b) by 311 days.

(21) Appl. No.: 15/545,496

(22) PCT Filed: Jan. 22, 2016

(86) PCT No.: PCT/JP2016/051925
§ 371 (c)(1),
(2) Date: Jul. 21, 2017

(87) PCT Pub. No.: WO2016/117700
PCT Pub. Date: Jul. 28, 2016

(65) Prior Publication Data
US 2018/0008981 A1  Jan. 11, 2018

(30) Foreign Application Priority Data

Jan. 22, 2015 (JP) ................................ 2015-010639

(51) Int. Cl.
*B01L 3/00* (2006.01)
*B01L 7/00* (2006.01)
(Continued)

(52) U.S. Cl.
CPC ........... *B01L 3/502753* (2013.01); *B01L 7/52* (2013.01); *G01N 21/07* (2013.01); *G01N 35/00069* (2013.01)

(58) Field of Classification Search
CPC ................. B01L 3/502753; B01L 7/52; G01N 35/00069; G01N 21/07; G01N 35/08;
(Continued)

(56) References Cited

U.S. PATENT DOCUMENTS 5,639,428 A * 6/1997 Cottingham ............ B01L 3/502
422/105
2004/0116686 A1 6/2004 Akashi et al.
(Continued)

FOREIGN PATENT DOCUMENTS

JP  H02-232563 A  9/1990
JP  2007-502428 A  2/2007
(Continued)

OTHER PUBLICATIONS

Koh et al "Centrifugal microfluidic platform for ultrasensitive detection of botulinum toxin." Anal Chem. Jan. 20, 2015; 87(2):922-8. (Year: 2015).*

(Continued)

*Primary Examiner* — Dennis White
(74) *Attorney, Agent, or Firm* — Morgan, Lewis & Bockius LLP

(57) ABSTRACT

The present invention provides a novel target analysis chip and analysis method for directly detecting a target such as a microRNA without performing PCR.

20 Claims, 7 Drawing Sheets

Specification includes a Sequence Listing.

(51) Int. Cl.
*G01N 21/07* (2006.01)
*G01N 35/00* (2006.01)

(58) Field of Classification Search
CPC ...... G01N 35/00; G01N 33/536; G01N 33/53; G01N 21/64; G01N 37/00; C12N 15/09; C12Q 1/68; C12M 1/00
See application file for complete search history.

(56) References Cited

U.S. PATENT DOCUMENTS

| | | |
|---|---|---|
| 2005/0014154 A1 | 1/2005 | Weizenegger |
| 2006/0278287 A1 | 12/2006 | Fielden et al. |
| 2009/0092989 A1 | 4/2009 | Chang et al. |

FOREIGN PATENT DOCUMENTS

| | | |
|---|---|---|
| JP | 2008-107227 A | 5/2008 |
| JP | 2008-196856 A | 8/2008 |
| JP | 2008-261831 A | 10/2008 |
| JP | 2011-500025 A | 1/2011 |
| JP | 5192229 B2 | 5/2013 |
| WO | 1999/051773 A1 | 10/1999 |
| WO | 1999/058245 A1 | 11/1999 |
| WO | 2002/097084 A1 | 12/2002 |
| WO | 2005/098029 A2 | 10/2005 |

OTHER PUBLICATIONS

Walsh et al, "A centrifugal fluidic immunoassay for ocular diagnostics with an enzymatically hydrolyzed fluorogenic substrate" Lab Chip. Aug. 7, 2014;14(15):2673-80 (Year: 2014).*
International Search Report issued in corresponding International Patent Application No. PCT/JP2016/051925 dated Apr. 12, 2016.
Koh et al., "Centrifugal Microfluidic Platform for Ultrasensitive Detection of Botulinum Toxin," Analytical Chemistry, 87: 922-928 (2014).
Walsh, III et al., "A centrifugal fluidic immunoassay for ocular diagnostics with an enzymatically hydrolyzed fluorogenic substrate," Lab Chip, 14: 2673-2680 (2014).
Extended European Search Report issued in corresponding European Patent Application No. 16740307.0 dated Jul. 5, 2018.
Office Action issued in corresponding Japanese Patent Application No. 2018-145075 dated Jul. 2, 2019.

* cited by examiner

TARGET ANALYSIS CHIP AND TARGET ANALYSIS METHOD

SEQUENCE LISTING SUBMISSION VIA EFS-WEB

A computer readable text file, entitled "SequenceListing.txt" created on or about Jul. 21, 2017, with a file size of about 1 kb contains the sequence listing for this application and is hereby incorporated by reference in its entirety.

TECHNICAL FIELD

The present invention relates to a target analysis chip and a target analysis method.

BACKGROUND ART

In recent years, the relationships between diseases and RNAs such as blood microRNAs have been drawing attention, and attempts have been made to utilize detection of RNAs in medical care for early disease detection and the like.

As a method of quantifying a microRNA, for example, there has been reported a method of specifically amplifying a target microRNA by polymerase chain reaction (PCR) and detecting the target microRNA (Japanese Patent No. 5192229). However, because of the necessity of performing PCR, for example, it is necessary to use a temperature-controlling apparatus and to perform reverse transcription into DNA, which makes the operations complicated. Moreover, in the above-described method, DNA is obtained from the RNA contained in a small amount of sample through reverse transcription and further amplified by PCR. Such reverse transcription PCR is, however, not direct detection but indirect detection of the RNA contained in the sample; therefore, there is a problem that the method is not sufficiently accurate for quantitative analysis.

SUMMARY OF INVENTION

Technical Problem

In view of the above, an object of the invention is to provide a novel target analysis chip and analysis method for directly detecting a target such as a microRNA, for example, without requiring PCR.

Solution of Problem

In order to solve the above-described problem, the target analysis chip according to the invention (hereinafter, also referred to as "analysis chip") includes a substrate, the substrate including a reaction section at which a sample containing a target is made to react with a reagent, a detection section at which label detection is performed, and a flow channel that communicates the reaction section with the detection section, in which:

the reagent includes a carrier;
the carrier includes a labeled probe immobilized thereon, the labeled probe being configured to bind to the target, and the carrier being configured to form a conjugate with the target;
the flow channel includes a movement controller configured to control movement of the carrier from the reaction section to the detection section;
the movement controller includes a hydrophobic inner wall in the flow channel; and
due to the movement controller, the conjugate is made to move to the detection section through the flow channel when a centrifugal force (C2), that is larger than a resistance force (R) caused by the hydrophobicity of the flow channel, is applied.

The target analysis method according to the invention (hereinafter, also referred to as "analysis method") uses the target analysis chip according to the invention, the target analysis method including:

introducing a sample and the reagent to the reaction section;
bringing the sample into contact with the carrier including a labeled probe immobilized thereon in the reaction section, thereby causing the target contained in the sample and the labeled probe to undergo a binding reaction and form a conjugate of the target and the labeled probe;
causing the conjugate in the reaction section to move to the detection section by a centrifugal force (C2) that is larger than a resistance force (R) caused by the hydrophobicity of the inner wall of the flow channel; and analyzing the target contained in the sample in the detection section by detecting the label of the labeled probe bound with the target.

Advantageous Effects of Invention

According to the invention, a target contained in a sample can be directly analyzed without using PCR. Further, in the invention in which the carrier having a labeled probe immobilized thereon is used, the flow channel includes the hydrophobic inner wall as the movement controller, and therefore the movement of the carrier from the reaction section to the detection section can be controlled. Further, by applying a centrifugal force (C2), that is larger than a resistance force (R) caused by the hydrophobicity of the inner wall of the flow channel, to a conjugate of the target and the labeled probe, for example, the conjugate can be recovered in the detection section in a highly concentrated state. Accordingly, in the analysis of a target contained in a sample, sufficient sensitivity and accuracy can be realized and, for example, the analysis can be performed even when the sample is applied to the target analysis chip in a very small amount. Therefore, the invention is considered to be useful, for example, in the medical field where targets such as microRNAs are analyzed.

BRIEF DESCRIPTION OF DRAWINGS

FIG. 1A is a perspective view; FIG. 1B is a top view, and FIG. 1C is a cross-sectional view taken along line I-I of FIG. 1A;

FIG. 4A is a perspective view, FIG. 4B is a top view, and FIG. 4C is a cross-sectional view taken along line I-I of FIG. 4A;

DESCRIPTION OF EMBODIMENTS

Figure 1A:
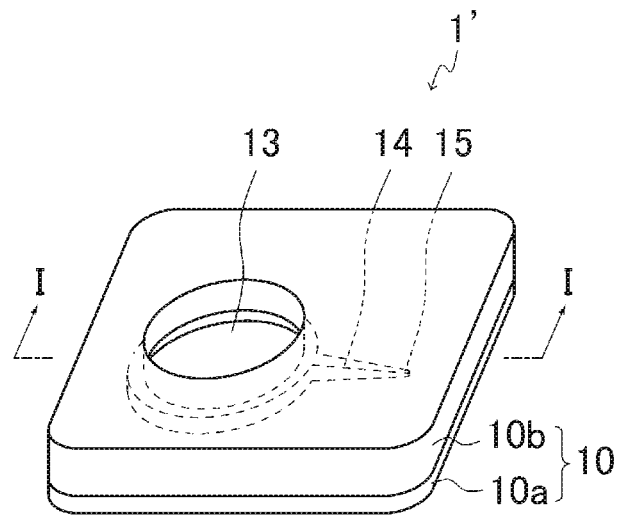
FIGS. 1A, 1B, and 1C are schematic views of one example of the target analysis chip according to the invention.

The analysis chip according to the invention includes, for example, the flow channel including a movement promoter configured to promote movement of the carrier from the reaction section toward the detection section.

In the analysis chip according to the invention, for example, the flow channel has a structure that the cross-sectional area thereof decreases in a direction from the reaction section toward the detection section.

In the analysis chip according to the invention, for example, the flow channel has a structure that narrows in a direction from the reaction section toward the detection section.

In the analysis chip according to the invention, for example, the inner wall of the detection section is hydrophobic.

In the analysis chip according to the invention, for example, a volume of an internal space of the detection section is smaller than a volume of the sample.

In the analysis chip according to the invention, for example, the detection section has a height of from 1 μm to 500 μm.

In the analysis chip according to the invention, for example, a volume of an internal space of the detection section is smaller than a volume of an internal space of the reaction section.

In the analysis chip according to the invention, for example, the carrier is a bead. The bead has a diameter of less than 100 μm, for example, or from 100 nm to 4 μm.

In the analysis chip according to the invention, for example, the carrier is made of silica.

In the analysis chip according to the invention, for example, a side surface of the flow channel is a curved surface that tapers from the reaction section toward the detection section.

In the analysis chip according to the invention, for example, a label of the labeled probe is a substance that exhibits a signal change upon binding of the labeled probe to the target.

In the analysis chip according to the invention, for example, the label is a substance containing pyrene.

In the analysis chip according to the invention, for example, the labeled probe is further modified with psoralen.

In the analysis chip according to the invention, for example, the target is a microRNA.

In the analysis chip according to the invention, for example, the amount of the labeled probe is from 1 zmol to 1 nmol.

In the analysis chip according to the invention, for example, the detection section is constituted by a light-transmitting member.

In the analysis chip according to the invention, for example, the reagent further includes a surfactant.

In the analysis chip according to the invention, for example, the reaction section also serves as a sample introduction section to which the sample is introduced.

In the analysis chip according to the invention, for example, the substrate further includes a sample introduction section to which the sample is introduced and a flow channel that communicates the sample introduction section with the reaction section, and the sample introduced to the sample introduction section is made to move to the reaction section by a centrifugal force (C1) that is smaller than the centrifugal force (C2).

In the analysis chip according to the invention, for example, the flow channel that communicates the sample introduction section with the reaction section further includes a filter.

In the analysis method according to the invention, for example, a mixture of the sample and the carrier is stirred in the reaction section.

In the analysis method according to the invention, for example, a label of the labeled probe is a substance that exhibits a signal change upon binding of the labeled probe to the target, and the signal change of the label is detected in the detection section.

In the analysis method according to the invention, for example, the label is a substance containing pyrene, and a fluorescence signal having a wavelength of from 450 nm to 510 nm is detected by irradiating the detection section with a UV light.

In the analysis method according to the invention, for example, the target to be analyzed is a microRNA.

1. Target Analysis Chip

The target analysis chip according to the invention includes a substrate, the substrate including a reaction section at which a sample containing a target is made to react with a reagent, a detection section at which label detection is performed, and a flow channel that communicates the reaction section with the detection section, in which the reagent includes a carrier;

the carrier includes a labeled probe immobilized thereon, and the labeled probe being configured to bind to the target, and the carrier being configured to form a conjugate with the target;

the flow channel includes a movement controller configured to control movement of the carrier from the reaction section to the detection section;

the movement controller includes a hydrophobic inner wall in the flow channel; and due to the movement controller, the conjugate is made to move to the detection section through the flow channel when a centrifugal force (C2), that is larger than a resistance force (R) caused by the hydrophobicity of the flow channel, is applied.

In the analysis chip according to the invention, the flow channel has the hydrophobic inner wall as the movement controller, and therefore the movement of the carrier from the reaction section to the detection section can be controlled. Therefore, for example, while spontaneous capillary action from the reaction section to the detection section is not generated, a capillary action is caused by a prescribed centrifugal force. As a result, the analysis chip according to the invention can also be said to be, for example, a chip in which, while spontaneous capillary action in the direction from the reaction section to the detection section is not generated, a capillary action is caused by a prescribed centrifugal force. In the analysis chip according to the invention, the carrier whose movement from the reaction section to the detection section is controlled may be, for example, a carrier forming the conjugate and/or a carrier not forming the conjugate, and preferably both of such carriers.

The analysis chip according to the invention is a chip used in the analysis method according to the invention, and the description in the analysis method according to the invention described as mentioned below can also be applied thereto. In the invention, the term "analysis" encompasses, for example, both qualitative analysis and quantitative analysis.

In the analysis chip according to the invention, the reaction section and the detection section are, for example, arranged sequentially in a single direction. In the analysis chip according to the invention, the direction that runs along the planar direction from the reaction section toward the detection section is also referred to as "longitudinal direction", or "movement direction" of the sample and the carrier; the direction that runs along the planar direction and is perpendicular to the longitudinal direction is also referred to as "width direction"; and the direction perpendicular to the planar direction (the direction perpendicular to both the longitudinal direction and the width direction) is also referred to as "thickness direction" or "depth direction". As described below, in a case in which the analysis chip according to the invention includes a sample introduction section, it is preferable that the sample introduction section, the reaction section, and the detection section in the analysis chip according to the invention are, for example, arranged sequentially in a single direction. In this case, in the analysis chip according to the invention, the direction that runs along the planar direction from the sample introduction section toward the detection section via the reaction section is also referred to as "longitudinal direction", or "movement direction" of the sample and the carrier. In the invention, the carrier including a labeled probe immobilized thereon is hereinafter also referred to as "analysis carrier". Further, in the invention, the flow channel that communicates the reaction section with the detection section is also referred to as "second flow channel", and the flow channel that communicates the sample introduction section with the reaction section is also referred to as "first flow channel".

First Embodiment

The analysis chip of the first embodiment has a configuration in which the reaction section also serves as a sample introduction section to which a sample is introduced. For example, the sample introduction section may be formed as an opening on the upper surface of the reaction section. In the analysis chip of the first embodiment, for example, since it is not necessary to provide the sample introduction section separately, the analysis chip can be made compact.

In the analysis chip of the first embodiment, the substrate may include, for example, a lower substrate and an upper substrate. In this case, for example, it is preferable that the reaction section, the second flow channel, and the detection section are formed by disposing the lower substrate and the upper substrate in layers.

A first specific example has a configuration in which the upper surface of the lower substrate (the surface on which the upper substrate is disposed) is flat; the upper substrate is provided with a through-hole that serves as an opening through which a sample is introduced to the reaction section; the lower surface of the upper substrate (the surface on which the lower substrate is disposed) is provided with a recess that constitutes the reaction section, the second flow channel, and the detection section; and the through-hole and the recess are communicated with each other. In this case, by disposing the lower substrate and the upper substrate in layers, the through-hole of the upper substrate and the upper surface of the lower substrate form the opening, and the recess of the upper substrate and the upper surface of the lower substrate form the reaction section, the second flow channel, and the detection section that are communicated with one another.

A second specific example has a configuration in which the lower surface of the upper substrate (the surface on which the lower substrate is disposed) is flat; the lower substrate is provided with a through-hole that serves as an opening through which a sample is introduced to the reaction section; the upper surface of the lower substrate (the surface on which the upper substrate is disposed) provided with a recess that constitutes the reaction section, the second flow channel, and the detection section; and the through-hole and the recess are communicated with each other. In this case, by disposing the lower substrate and the upper substrate in layers, the through-hole of the lower substrate and the lower surface of the upper substrate form the opening, and the recess of the lower substrate and the lower surface of the upper substrate form the reaction section, the second flow channel, and the detection section that are communicated with one another.

In the analysis chip of the first embodiment, the size and the shape of the reaction section are not particularly restricted.

The reaction section has, for example, a configuration in which the bottom surface thereof is formed by the upper surface of the lower substrate and the upper surface thereof is formed by the lower surface of the upper substrate. The reaction section has, for example, a hollow columnar shape (which is also referred to as "tubular shape"). Specifically, the reaction section preferably has a columnar shape whose axial direction coincides with the thickness direction of the analysis chip. Examples of the columnar shape include a cylindrical shape and a prismatic shape. The reaction section may be provided with, for example, an air hole, and the air hole can be formed as a through-hole or the like on the upper substrate on the upper surface side of the reaction section.

In the analysis chip of the first embodiment, the second flow channel has, for example, a configuration in which the bottom surface thereof is formed by the upper surface of the lower substrate, and the upper surface thereof is formed by the lower surface of the upper substrate. The second flow channel has a hollow shape, specifically a hollow shape whose axial direction coincides with the longitudinal direction of the analysis chip. In the second flow channel, a cross-section perpendicular to the axial direction (hollow cross-section) has, for example, a circular shape such as a perfect circular shape or an elliptical shape; or a polygonal shape such as a square shape or a rectangular shape.

It is preferable that the second flow channel includes, for example, a movement promoter configured to promote movement of the analysis carrier from the reaction section to the detection section. In a case in which the second flow channel includes the movement promoter, for example, the analysis carrier can be efficiently moved and recovered in the detection section. The movement promoter in the second flow channel is not particularly restricted and, for example, as described below, the movement promoter may have a structure in which the cross-sectional area thereof decreases in a direction from the reaction section toward the detection section.

Examples of the structure of the second flow channel include one in which the cross-sectional area thereof decreases in a direction from the reaction section toward the detection section. This structure can also be said to be a structure that is constricted in a direction from the reaction section toward the detection section. The cross-sectional area of the second flow channel is the area of a cross-section perpendicular to the longitudinal direction of the analysis chip, which is the area of a hollow cross-section of the second flow channel.

For example, the cross-sectional area may decrease continuously or non-continuously (stepwise) in a direction from the reaction section toward the detection section. As a specific example, in the second flow channel, for example, the shape of a cross-section parallel to the axial direction may taper from the reaction section toward the detection section. Specifically, in the second flow channel, for example, a cross-section viewed from a lateral side of the analysis chip may have a shape that tapers from the reaction section toward the detection section, and/or a cross-section viewed from the upper surface (or the lower surface) of the analysis chip has a shape that tapers from the reaction section toward the detection section.

It is preferable that a side surface of the second flow channel is, for example, a curved surface that tapers from the reaction section toward the detection section. In a case in which the side surface of the second flow channel has such a shape, the analysis carrier can be efficiently moved and recovered in the detection section. The radius of curvature (R) of the curved surface is, for example, from 1 mm to 5 mm, from 1.5 mm to 4.5 mm, or about 3 mm (e.g., from 2.5 mm to 3.5 mm), since the analysis carrier can be more efficiently recovered in the detection section. The radius of curvature (R) of the curved surface is, for example, the radius of curvature of the above-described tapering curved surface.

As described above, the second flow channel includes a movement controller configured to control movement of the analysis carrier from the reaction section to the detection section. Due to the movement controller, a conjugate in the reaction section (the carrier forming a conjugate) is made to move to the detection section through the second flow channel, when a centrifugal force (C2), that is larger than a resistance force (R) caused by the hydrophobicity of the flow channel, is applied. Specifically, in a case in which the second flow channel has a hydrophobic inner wall as the movement controller, when a centrifugal force (C2), that is larger than a resistance force (R) caused by the hydrophobicity of the flow channel, is not applied to the conjugate, spontaneous capillary action in the direction from the reaction section to the detection section is not generated and therefore the analysis carrier can be retained in the reaction section for example. Meanwhile, when a centrifugal force (C2) that is larger than the resistance force (R) is applied to the conjugate, capillary action in the direction from the reaction section to the detection section is generated and therefore the conjugate is made to move from the reaction section to the detection section. Thus, in the analysis chip according to the invention, the term "hydrophobicity" means, for example, such hydrophobicity at a level that does not cause the movement of a liquid fraction from the reaction section to the detection section by spontaneous capillary action. In the present invention, for example, when the centrifugal force (C2) is applied, the analysis carrier not forming the conjugate as well as the conjugate is caused to move to the detection section through the flow channel. For example, in a case in which the second flow channel is constituted by a hydrophobic member as described below, hydrophobicity can be imparted by the hydrophobic inner wall of the second flow channel. In the second flow channel, for example, the entire inner wall of the lower, upper, and side surfaces may be hydrophobic, or the inner wall may be partially hydrophobic. Specifically, in a case in which the analysis chip is formed by an upper substrate and a lower substrate, for example, the inner wall of the second flow channel that is formed by the upper substrate may be hydrophobic, or the inner wall of the second flow channel that is formed by the lower substrate may be hydrophobic, or the inner wall of the second flow channel that is formed by the upper substrate and the lower substrate may be hydrophobic. In the analysis chip of the first embodiment, the inner wall of the detection section may also be hydrophobic, and the movement controller may include the hydrophobic inner wall of the detection section. The details of resistance force (R) and the centrifugal force (C2) are described below.

The size of the internal space of the second flow channel is not particularly restricted. The height (depth) of the second flow channel is, for example, from 1 μm to 3,000 μm, or from 100 μm to 500 μm. The width of the second flow channel is, for example, from 1 μm to 3,000 μm, or from 100 μm to 500 μm. The height and the width of the second flow channel are, for example, the height and the width of the internal space of the second flow channel, respectively.

In the analysis chip of the first embodiment, the shape of the detection section is not particularly restricted. The detection section has, for example, a hollow shape, and may be an extension of the second flow channel. That is, in the analysis chip according to the invention, the detection section may be, for example, a terminal region of the second flow channel that is communicated with the reaction section, on the side opposite to the reaction section. The shape of the detection section is not particularly restricted, and its cross-section perpendicular to the axial direction (e.g., a hollow cross-section) has, for example, a circular shape such as a perfect circular shape or an elliptical shape; or a polygonal shape such as a square shape or a rectangular shape.

It is preferable that a volume of an internal space of the detection section is smaller than, for example, a volume of the sample. In a case in which the volume of the detection section is designed to be small relative to, for example, the volume of the sample, the concentration of the analysis carrier in the detection section can be set relatively high. The volume of the internal space of the detection section is, for example, from $1/1\times10^2$ to $1/1\times10^6$ (e.g., $1/1\times10^4$) with respect to the volume of the sample. Further, the lower limit of the volume of the detection section is preferably larger than, for example, the total volume of the analysis carrier arranged in the reaction section. It is also preferable that the volume of the internal space of the detection section is smaller than, for example, the volume of the internal space of the reaction section. In a case in which the volume of the detection section is designed to be small relative to, for example, the volume of the internal space of the reaction section, the concentration of the analysis carrier in the detection section can be set relatively high. The volume of the internal space of the detection section is, for example, from $1/1\times10$ to $1/1\times10^6$, or from $1/1\times10^2$ to $1/1\times10^5$ (e.g., $1/1\times10^4$), with respect to the volume of the internal space of the reaction section. The height (depth) of the detection section is not particularly restricted, and is, for example, from 1 μm to 3,000 μm, from 10 μm to 300 μm, or about 100 μm (e.g., from 50 μm to 150 μm). In a case in which the height of the detection section is set in the above range, for example, the ratio of the detectable label is further increased in the carrier moved to the detection section. The width of the detection section is not particularly restricted, and is, for example, from 1 μm to 3,000 μm, or from 10 μm to 300 μm. The height and the width of the detection section are, for example, the height and the width of the internal space of the detection section, respectively.

In the analysis chip of the first embodiment, as described above, the reaction section includes a carrier that includes a labeled probe immobilized thereon, and the labeled probe is configured to bind to the target (the above-described analysis carrier). Further, the analysis carrier is a carrier that is configured to form a conjugate with the below-described target. The labeled probe is a probe modified with a labeling substance (hereinafter, also referred to as "label"). Examples of the probe include an RNA, a DNA, and RNA/DNA, and the probe is preferably an RNA. The RNA may be, for example, an unmodified RNA or a modified RNA, or the RNA may contain both thereof. Examples of the modified RNA include 2'-O-methyl RNA. The DNA may be, for example, a modified DNA or an unmodified DNA, or the DNA may contain both thereof. The probe may contain, for example, an artificial nucleic acid monomer. Examples of the artificial nucleic acid monomer include PNAs (peptide nucleic acids), LNAs (locked nucleic acids), and ENAs (2'-0,4'-C-ethylene bridged nucleic acids). The method of modifying the probe with the labeling substance is not particularly restricted, and any known method can be employed. The probe can be designed as appropriate based on, for example, the target to be analyzed. In a case in which the target is the above-described target nucleic acid, examples of the sequence of the labeled probe include those sequences that are partially or completely complementary to the target nucleic acid. The labeling position of the labeled probe is not particularly restricted and, for example, the labeled probe may be labeled at a base of the 3'-end, at a base of the 5'-end, or at any other base.

The labeling substance is not particularly restricted, and may be, for example, a fluorescent labeling substance or a radioactive labeling substance. The fluorescent labeling substance is not particularly restricted, and examples thereof include fluorescent substances such as fluorophores. Examples of the fluorescent labeling substance also include fluoresceins, phosphors, rhodamines, and polymethine dye derivatives. Examples of commercially available fluorescent labeling substances include PACIFIC BLUE (registered trademark, manufactured by Molecular Probes, Inc.), BODIPY FL (registered trademark, manufactured by Molecular Probes, Inc.), FLUOREPRIME (trade name, manufactured by Amersham Pharmacia Biotech Inc.), FLUOREDITE (trade name, manufactured by Millipore Corporation), FAM (registered trademark, manufactured by Applied Biosystems, Inc. (ABI)), Cy3 and Cy5 (trade name, manufactured by Amersham Pharmacia Biotech Inc.), and TAMRA (registered trademark, manufactured by Molecular Probes, Inc.).

In a case in which the labeled probe is a fluorescently labeled probe that is labeled with the fluorescent labeling substance, it is preferable that the fluorescent labeling substance of the fluorescently labeled probe is, for example, a substance that exhibits a signal change upon binding of the fluorescently labeled probe to the target (e.g., target nucleic acid or target RNA). The signal is, for example, a fluorescence signal. In a case in which such a fluorescent label is used, for example, it is not necessary to separate the fluorescently labeled probe that is bound with the target from the fluorescently labeled probe that is not bound with the target, and thus analysis accuracy can be further improved and analysis further simplified.

Specific examples of the fluorescent labeling substance include a substance containing pyrene (hereinafter, also referred to as "pyrene-containing substance"). The fluorescent labeling substance may be, for example, a pyrene-containing substance, or pyrene itself. When the fluorescent labeling substance is a pyrene-containing substance, the description of Japanese Patent No. 4238381 can be applied to the design of the fluorescently labeled probe. It is preferable that the pyrene-containing substance modifies, for example, a uridine residue and/or a cytidine residue and, specifically, it is preferable that the pyrene-containing substance is covalently bound to the hydroxyl group at the 2'-position of a uridine residue and/or the hydroxyl group at the 2'-position of a cytidine residue. The fluorescently labeled probe is preferably, for example, an RNA that contains uridine to which the pyrene-containing substance is covalently bound, or a DNA or DNA/RNA that contains uridine and/or cytidine to which the pyrene-containing substance is covalently bound. For example, the fluorescently labeled probe modified with the pyrene-containing substance binds to the target nucleic acid (e.g., target RNA) to form a double-stranded structure, thereby emitting fluorescence. Therefore, the target nucleic acid can be analyzed by detecting a signal of the fluorescence. The fluorescence can be emitted by, for example, exciting the label by UV light irradiation. The wavelength of the irradiated light is, for example, from 325 nm to 350 nm (e.g., 340 nm), and the fluorescence detection wavelength is, for example, from 450 nm to 510 nm (e.g., 480 nm).

It is preferable that the fluorescently labeled probe is further modified with, for example, psoralen. In a case in which the fluorescently labeled probe has psoralen, for example, irradiation of a UV light to a double strand formed by the fluorescently labeled probe and the target nucleic acid causes, in the double strand, psoralen of the fluorescently labeled probe to covalently bind with a uracil residue in the target nucleic acid. As a result, the bond of the double strand of the target nucleic acid and the fluorescently labeled probe can be further stabilized; therefore, for example, dissociation of the target nucleic acid from the fluorescently labeled probe can be sufficiently inhibited even during the below-described various treatments of the analysis chip, and the sensitivity can be further improved.

The carrier including a labeled probe immobilized thereon is not particularly restricted, and examples thereof include a carrier that has a specific gravity of greater than 1 and are formed from a light-transmitting material. Specific examples of the carrier include a silica-gel carrier, a silica carrier, an agarose carrier, a glass carrier (e.g., a borosilicate glasscarrier, a lime glasscarrier), a polystyrene carrier, an acrylic resin carrier, a polyvinyl alcohol resin carrier, and a polycarbonate carrier. The carrier may also be, for example, a magnetic carrier. In a case in which the carrier is a magnetic carrier, for example, since the magnetic carrier is caused to move in the reaction section by a magnetic force, a mixture of the sample and the analysis carrier can be stirred in the reaction section as described below. The size of the carrier is not particularly restricted. Further, the shape of the carrier is not particularly restricted and may be, for example, a spherical shape such as an elliptical shape or a perfect circular shape. Specific examples of the carrier include a bead such as a spherical bead. In a case in which the carrier is the bead, the lower limit of the diameter thereof is, for example, 0.1 µm (100 nm), 200 nm, 250 nm, or 300 nm, and the upper limit of the diameter thereof is, for example, less than 100 µm, 10 µm or less, 5 µm or less, 4 µm or less, 1 µm or less, 800 nm or less, or 400 nm or less, and the range of the diameter thereof is, for example, in a range of from 100 nm to 4 µm, from 100 nm to 800 nm, from 0.2 µm to 0.8 µm, or from 250 nm to 400 nm. In a case in which the detection section has a height of from 1 µm to 500 µm, the diameter of the carrier is preferably, for example, from 100 nm to 4 µm, from 100 nm to 800 nm, or from 250 nm to 400 nm, since the ratio of the carrier that is made to move to the detection section is increased and the ratio of the detectable label is further increased.

In the analysis carrier, the amount of the labeled probe to be immobilized on the carrier is not particularly restricted and can be set as appropriate in terms of, for example, the amount per surface area of the carrier. Further, the amount of the labeled probe to be arranged on the analysis chip is not particularly restricted and can be set as appropriate in accordance with, for example, the amount of the target contained in the sample. The amount of the labeled probe is, for example, from 1 zmol to 1 nmol, from 1 amol to 100 pmol, or from 10 amol to 10 pmol. Further, the amount of the analysis carrier to be arranged in the reaction section is not particularly restricted and can be set as appropriate in terms of, for example, the amount per bottom area of the reaction section.

The analysis chip according to the invention may include, for example, the analysis carrier as the reagent. For example, the analysis chip according to the invention may include the analysis carrier separately from the analysis chip, or may include the analysis carrier in the analysis chip. In the former case, the analysis chip according to the invention may also be referred to as, for example, "target analysis kit". In the latter case, for example, the reaction section includes the analysis carrier. In this case, for example, the analysis carrier may be in a free state in the reaction section. Alternatively, for example, the analysis carrier may be in a state of being releasably immobilized in the reaction section (on the inner wall of the reaction section). In the latter case, it is preferable that the analysis carrier is immobilized in the reaction section by, for example, a water-soluble material. In this case, for example, the sample introduced through the opening of the reaction section causes the analysis carrier to be released from the reaction section (from the inner wall of the reaction section). Examples of the water-soluble material include polyvinyl alcohols; cellulose derivatives such as carboxymethylcellulose or methylcellulose; water-soluble polymers such as polyacrylic polymers, polyacrylamides, polyethylene oxides, starch, or gelatin; and oligosaccharides such as sucrose, trehalose, mannitol, or lactose.

The analysis chip of the first embodiment may further include, for example, other substance as the reagent, in addition to the analysis carrier. The other substance is not particularly restricted, and examples thereof include a surfactant, a buffer, a salt, a water-soluble polymer, and a saccharide. Examples of the surfactant include a nonionic surfactant and an ionic surfactant, and the surfactant is preferably a nonionic surfactant since it facilitates the reaction between the target and the labeled probe. Examples of the nonionic surfactant include TWEEN 20 (registered trademark), TRITON (trademark) X-100, sucrose fatty acid esters, sorbitan fatty acid esters, polyoxyethylene sorbitan fatty acid esters, fatty acid alkanolamides, polyoxyethylene alkyl ethers, and polyoxyethylene alkylphenyl ethers.

In the analysis chip according to the invention, the reaction section may further include a stirring element. In this case, in the reaction section, by stirring a mixture of the sample and the analysis carrier arranged in the reaction section using the stirring element, the target contained in the sample and the labeled probe immobilized on the analysis carrier can be efficiently brought into contact with each other. As the stirring element, for example, a magnetic stirring element can be used, and specific examples thereof include stirrers such as magnetic beads. The material of the stirring element is not particularly restricted; however, the stirring element is preferably made of a magnetic material such as SUS. The stirring element has a shape of, for example, a sphere having a diameter size of, for example, from 0.1 mm to 5 mm (e.g., 1 mm).

In the analysis chip according to the invention, the material of the substrate is not particularly restricted and may be a glass such as quartz glass or borosilicate glass or a resin such as PDMS (polydimethylsiloxane), polystyrene, acrylic resin, cycloolefin resin, or polyethylene terephthalate, and it is preferable to use the hydrophobic member as described below. Further, in a case in which the substrate includes the lower substrate and the upper substrate as described above, for example, both of the substrates may be made of the same material, or the substrates may be made of different materials.

In the analysis chip of the first embodiment, the detection section is formed by, for example, a light-transmitting member, preferably a UV-transmitting member. Examples of the light-transmitting member include glasses such as quartz glass or boronsilicate glass, and resins such as PDMS.

In the analysis chip of the first embodiment, as described above, the inner wall of the second flow channel is hydrophobic. The hydrophobic inner wall may be formed, for example, by using a hydrophobic member as the substrate, by disposing a hydrophobic member on the surface of the substrate, or by modifying the surface of the substrate to be hydrophobic. Examples of the hydrophobic member include hydrophobic resins such as PDMS (polydimethylsiloxane), polystyrene, acrylic resins, cycloolefin resins, or fluorocarbon resins. The method of modifying the surface of the substrate to be hydrophobic is not particularly restricted, and any known method can be employed.

Second Embodiment

The analysis chip of the second embodiment has a configuration in which a sample introduction section to which a sample is introduced is provided separately from the reaction section. In the analysis chip of the second embodiment, for example, the first flow channel that communicates the sample introduction section with the reaction section; and the condition (3) described below is satisfied. According to the analysis chip of the second embodiment, for example, a target analysis can be simply performed by two centrifugation processes. In the analysis chip of the second embodiment, for example, the substrate further includes a flow channel that communicates the reaction section with the sample introduction section to which the sample is introduced. The analysis chip of the second embodiment can also be said to be an analysis chip in which the sample introduced to the sample introduction section is caused to move to the reaction section by a centrifugal force (C1) that is smaller than the centrifugal force (C2). Further, according to the analysis chip of the second embodiment, by arranging a filter in the first flow channel, a sample containing a contaminant can also be analyzed without the removal of the contaminant by a pretreatment.

(3) A sample introduced to the sample introduction section is caused to move to the reaction section by a centrifugal force (C1) but the carrier in the reaction section is not substantially moved to the detection section by the centrifugal force (C1).

The analysis chip of the second embodiment is the same as the analysis chip of the first embodiment, except that the reaction section has no opening and the sample introduction section and the first flow channel are provided. Thus, unless otherwise specified, the descriptions of the analysis chip of the first embodiment can be applied to the analysis chip of the second embodiment.

In the analysis chip of the second embodiment, the substrate may include, for example, a lower substrate and an upper substrate. In this case, for example, it is preferable that the sample introduction section, the first flow channel, the reaction section, the second flow channel, and the detection section are formed by disposing the lower substrate and the upper substrate in layers.

A first specific example has a configuration in which the upper surface of the lower substrate (the surface on which the upper substrate is disposed) is flat; the upper substrate is provided with a through-hole that serves as the sample introduction section; the lower surface of the upper substrate (the surface on which the lower substrate is disposed) is provided with a recess that constitutes the first flow channel, the reaction section, the second flow channel, and the detection section; and the through-hole and the recess are communicated with each other. In this case, by disposing the lower substrate and the upper substrate in layers, the through-hole of the upper substrate and the upper surface of the lower substrate form the sample introduction section, and the recess of the upper substrate and the upper surface of the lower substrate form the first flow channel, the reaction section, the second flow channel, and the detection section that are communicated with one another.

A second specific example has a configuration in which the lower surface of the upper substrate (the surface on which the lower substrate is disposed) is flat; the lower substrate is provided with a through-hole that serves as the sample introduction section; the upper surface of the lower substrate (the surface on which the upper substrate is disposed) is provided with a recess that constitutes the first flow channel, the reaction section, the second flow channel, and the detection section; and the through-hole and the recess are communicated with each other. In this case, by disposing the lower substrate and the upper substrate in layers, the through-hole of the lower substrate and the lower surface of the upper substrate form the sample introduction section, and the recess of the lower substrate and the lower surface of the upper substrate form the first flow channel, the reaction section, the second flow channel, and the detection section that are communicated with one another.

In the analysis chip according to the invention, the size and the shape of the sample introduction section, the reaction section, and the first flow channel are not particularly restricted.

The sample introduction section has, for example, a configuration in which the bottom surface thereof is formed by the upper surface of the lower substrate and the upper part thereof is opened by the through-hole of the upper substrate. The sample introduction section has, for example, a hollow columnar shape (which is also referred to as "tubular shape") with a closed bottom. Specifically, the sample introduction section preferably has a columnar shape whose axial direction coincides with the thickness direction of the analysis chip. Examples of the columnar shape include a cylindrical shape and a prismatic shape.

The reaction section has, for example, a configuration in which its bottom surface thereof is formed by the upper surface of the lower substrate and the upper surface thereof is formed by the lower surface of the upper substrate. The reaction section has, for example, a hollow columnar shape (which is also referred to as "tubular shape"). Specifically, the reaction section preferably has a columnar shape whose axial direction coincides with the thickness direction of the analysis chip. Examples of the columnar shape include a cylindrical shape and a prismatic shape. The reaction section may be provided with, for example, an air hole, and the air hole can be formed as a through-hole or the like on the upper substrate on the upper surface side of the reaction section.

The first flow channel that communicates the sample introduction section with the reaction section has, for example, a configuration in which the bottom surface thereof is formed by the upper surface of the lower substrate and the upper surface thereof is formed by the lower surface of the upper substrate. The first flow channel has a hollow shape, specifically a hollow shape whose axial direction coincides with the longitudinal direction of the analysis chip. In the first flow channel, a cross-section perpendicular to the axial direction (hollow cross-section) has, for example, a circular shape, such as a perfect circular shape or an elliptical shape; or a polygonal shape, such as a square shape or a rectangular shape.

The first flow channel may further include, for example, a filter. In a case in which the he first flow channel includes the filter, for example, even a sample such as a sample containing a contaminant can be analyzed without the removal of the contaminant by a pretreatment. The type of the filter is not particularly restricted, and examples of the filter include those having a fiber structure, such as filter papers, nonwoven fabrics, or glass fibers; those having a spongy porous structure; and those having a porous membrane structure. The position at which the filter is arranged in the first flow channel is not particularly restricted, and the filter can be arranged at any position.

As described above, the analysis chip according to the invention is, for example, set on a centrifuge and applied to a centrifugal force. Therefore, it is preferable that the analysis chip according to the invention further includes a part for arrangement on the centrifuge.

The sample introduced to the analysis chip according to the invention is a sample containing a target, but the invention is not restricted thereto. The sample may be, for example, a target-free sample, or a sample for which it is unclear if it contains a target or not. The form of the sample is not particularly restricted, and the sample is, for example, a liquid sample. The liquid sample may be, for example, a specimen derived from a living body, or a dilution, suspension or the like of the specimen. Examples of the specimen include body fluids such as blood, urine, gastric fluid, sputum, amniotic fluid, or peritoneal fluid; tissues such as large intestine or lung; and cells such as intraoral cells, germ cells, nail cells, or hair cells. Examples of the blood include whole blood, plasma, serum, and hemolysate. For example, the liquid sample may be used after a pretreatment. The pretreatment is not particularly restricted, and examples thereof include a treatment for causing a target (e.g., a nucleic acid such as DNA or RNA) to be released from the cells contained in the specimen.

The amount of the sample to be introduced to the analysis chip according to the invention is not particularly restricted, and is, for example, 1 µL to 100 µL (e.g., 50 µL) per analysis chip.

The type of the target to be analyzed by the analysis chip according to the invention is not particularly restricted, and the target may be, for example, a target nucleic acid. Examples of the target nucleic acid include target RNAs and target DNAs. Examples of the target RNAs include microRNAs, virus-derived RNAs, and messenger RNAs. Examples of the target DNAs include DNAs derived from cells contained in blood, such as genomic DNAs or fragments thereof, cDNAs, free DNAs in blood, or circulating tumor cells in blood.

2. Target Analysis Method

As described above, the target analysis method according to the invention uses the target analysis chip according to the invention, and the method includes:

introducing a sample and the reagent to the reaction section (introduction process);

bringing the sample into contact with the carrier including a labeled probe immobilized thereon in the reaction section, thereby causing the target contained in the sample and the labeled probe to undergo a binding reaction and form a conjugate of the target and the labeled probe (reaction process);

causing the conjugate in the reaction section to move to the detection section by a centrifugal force (C2) that is larger than a resistance force (R) caused by the hydrophobicity of the inner wall of the flow channel (carrier-moving process); and analyzing the target contained in the sample in the detection section by detecting the label of the labeled probe bound with the target (analysis process).

The target analysis method according to the invention is a method that uses the target analysis chip according to the invention, and the descriptions in the target analysis chip according to the invention as mentioned above can also be applied thereto. For example, the target analysis method according to the invention does not include a PCR process.

In the introduction process, as described above, the sample and the reagent are introduced to the reaction section. In the introduction process, for example, the sample and the reagent are introduced through an opening of the reaction section of the analysis chip. The order of introducing the sample and the reagent is not particularly restricted and, for example, the reagent may be introduced before or after the sample is introduced, or the sample and the reagent may be introduced simultaneously. As described above, in a case in which the reaction section includes the analysis carrier, in the introduction process, for example, only the sample instead of the sample and the reagent is introduced. Further, in a case in which the analysis carrier is immobilized in the reaction section as described above, the introduction of the sample causes, for example, the immobilization of the analysis carrier to be cancelled and the analysis carrier to be thereby released.

In a case in which the analysis chip includes the sample introduction section separately from the reaction section, the analysis method may include, for example, the process of introducing a sample to the sample introduction section (sample introduction process) and the process of causing the sample introduced to the sample introduction section to move to the reaction section by a centrifugal force (C1) that is smaller than the centrifugal force (C2) (sample-moving process), in place of the introduction process. In the sample introduction process, for example, the sample is introduced through an opening of the sample introduction section of the analysis chip.

In the sample-moving process, for example, as described above, the sample introduced to the sample introduction section is caused to move to the reaction section by a centrifugal force (C1). The centrifugal force (C1) is, for example, a centrifugal force that is smaller than the centrifugal force (C2) applied in the subsequent carrier-moving process. By controlling the centrifugal force (C1) to be smaller than the centrifugal force (C2), for example, the analysis carrier in the reaction section is not substantially moved to the detection section. The lower limit of the centrifugal force (C1) is not particularly restricted. In a case in which the analysis carrier is immobilized in the reaction section as described above, the introduction of the sample causes, for example, the immobilization of the analysis carrier to be cancelled and the analysis carrier to be thereby released.

In the invention, for example, a centrifuge can be used to apply a centrifugal force to the analysis chip. In this case, it is preferable that the analysis chip further includes, for example, a part for arrangement on the centrifuge. For example, the analysis chip is set on the centrifuge through the part for arrangement, and a centrifugal force can be applied to the analysis chip using the centrifuge.

In the reaction process, the sample is brought into contact with the carrier including a labeled probe immobilized thereon in the reaction section as described above, thereby causing the target contained in the sample and the labeled probe to undergo a binding reaction and form a conjugate of the target and the labeled probe. In this process, it is preferable that, for example, a mixture of the carrier and the sample introduced to the reaction section or a mixture of the carrier and the sample moved from the sample introduction section is stirred in the reaction section. The stirring method is not particularly restricted.

Examples of the stirring method include a method of using the stirring element. In this case, it is preferable that the reaction section of the analysis chip further includes the stirring element and that the mixture is stirred in the reaction section by the stirring element. The stirring using the stirring element can be performed by, for example, arranging a magnet outside the analysis chip and moving the stirring element using the magnet. The stirring element may be, for example, rotated about its axis, revolved, or randomly moved.

Examples of the stirring method also include a method of using a magnetic carrier as a carrier on which the labeled probe is immobilized as described above. In this case, the magnetic carrier on which the labeled probe is immobilized can be used in the same manner as the stirring element. Specifically, stirring can be performed by arranging a magnet outside the analysis chip and moving the magnetic carrier using the magnet. The magnetic carrier may be, for example, rotated about its axis, revolved, or randomly moved.

Examples of the stirring method also include a method of utilizing a centrifuge. For example, as described above, since a centrifugal force is utilized for the movement of the sample from the sample introduction section to the reaction section or the movement of the carrier from the reaction section to the detection section, the analysis chip can be used by setting on a centrifuge for use. Accordingly, in the reaction process, stirring can also be performed by centrifuging the analysis chip. The centrifugation may be, for example, centrifugation performed in a single direction, or centrifugation performed alternately in two opposite directions.

In the reaction process, the conditions (e.g., temperature, time, etc.) for bringing the sample and the analysis carrier into contact are not particularly restricted.

The carrier-moving process is, as described above, the process of causing the conjugate in the reaction section to move to the detection section by a centrifugal force (C2), that is larger than a resistance force (R) caused by the hydrophobicity of the inner wall of the flow channel. Further, since the centrifugal force (C2) is larger than the centrifugal force (C1) as described above, the carrier-moving process can also be said to be, for example, the process of causing the conjugate in the reaction section to move to the detection section by the centrifugal force (C2) that is larger than the centrifugal force (C1).

The resistance force (R) can be calculated as appropriate based on, for example, the degree of the hydrophobicity of the inner wall of the second flow channel. As a specific example, the resistance force (R) can be calculated from, for example, the surface tension of the mixture of the sample and the reagent, the contact angle between the inner wall of the second flow channel and the mixture of the sample and the reagent, and the width and the height of the second flow channel of the analysis chip, and specifically, the resistance force (R) is represented by Equation (1) below. In a case in which the contact angle (θ) between the inner wall of the second flow channel and the mixture of the sample and the reagent is 90° or larger, the resistance force (R) can be suitably calculated by, for example, the following Equation (1).

$$R = -2wh\gamma \cos\theta(1/w + 1/h) \quad \text{Equation (1):}$$

R: Resistance force (N)
γ: Surface tension of the mixture of the sample and the reagent (N/m)
θ: Contact angle between the inner wall of the second flow channel and the mixture of the sample and the reagent
w: Width of the second flow channel (m)
h: Height of the second flow channel (m)

The centrifugal force (C2) is not particularly restricted as long as, for example, the conjugate is caused to move to the detection section. In the analysis method according to the invention, the mixture of the sample and the reagent is introduced to the second flow channel by, for example, the centrifugal force (C2). Further, by the centrifugal force (C2), for example, the analysis carrier (e.g., conjugate) contained in the mixture is accumulated in one opposite end of the detection section in the analysis chip from the second flow channel. In this case, the time (Δt) required for the analysis carrier to be accumulated in the detection section can be calculated from, for example, the viscosity and density of the mixture, the density of the analysis carrier, the radius of the analysis carrier, the rotational speed during centrifugation, and the starting and end points of the radius of rotation. Specifically, the time (Δt) is represented by the following Equation (2). According to Equation (2), for example, the density and radius of the analysis carrier and the centrifugal force (C2), namely the radius of rotation and the rotational speed (angular velocity of rotation), required for accumulating the analysis carrier in the detection section within a desired centrifugation time can be calculated (estimated).

$$\Delta t = [18\mu/(4\omega^2 R^2(\rho s - \mu 1))] \ln(r2/r1) \quad \text{Equation (2):}$$

Δt: Time required for the analysis carrier to move from the starting point (r1) of the radius of rotation to the end point (r2) of the radius of rotation (sec)
μ: Viscosity of the mixture of the sample and the reagent (Pa×s)
ρ1: Density of the mixture of the sample and the reagent (kg/m³)
ρs: Density of the analysis carrier (kg/m³)
R: Radius of the analysis carrier (m)
ω: Angular velocity of rotation (rad/sec)
r1: Starting point of the radius of rotation (the shortest distance between the axis and the reaction section during centrifugation) (m)
r2: End point of the radius of rotation (the longest distance between the axis and the detection section) (m)

The analysis process is a process of detecting the label of the labeled probe bound with the target in the detection section to analyze the target contained in the sample. The detection of the label is not particularly restricted and can be determined as appropriate in accordance with, for example, the type of the label.

As described above, it is preferable that the label of the labeled probe is, for example, a substance that exhibits a signal change upon binding of the labeled probe to the target. In this case, in the analysis process, for example, the signal change of the label is detected in the detection section. As a specific example, in a case in which the label is the above-described pyrene-containing substance, the detection section is irradiated with a UV light, and the fluorescence signal from pyrene is detected. The conditions for detecting the fluorescence signal are, for example, as described above.

As other embodiments according to the invention, specific examples of the analysis chip according to the invention and the analysis method according to the invention using the analysis chip is described hereinbelow by reference to the drawings. Here, analysis methods in which the analysis chip of the first embodiment or the analysis chip of the second embodiment is used as the analysis chip, the fluorescently labeled probe is used as the labeled probe, and a target RNA as the target is analyzed, are described as examples. However, the invention is not restricted thereto.

Third Embodiment

The third embodiment is one example of the analysis method, in which the analysis chip of the first embodiment is used, the fluorescently labeled probe is used as the labeled probe, the reagent is arranged in the reaction section, and a target RNA as the target is analyzed. It is noted here that, in FIGS. 1A, 1B, 1C, 2, 3, 4A, 4B, and 4C described below, the same parts are assigned with the same symbols.

Figure 1B:
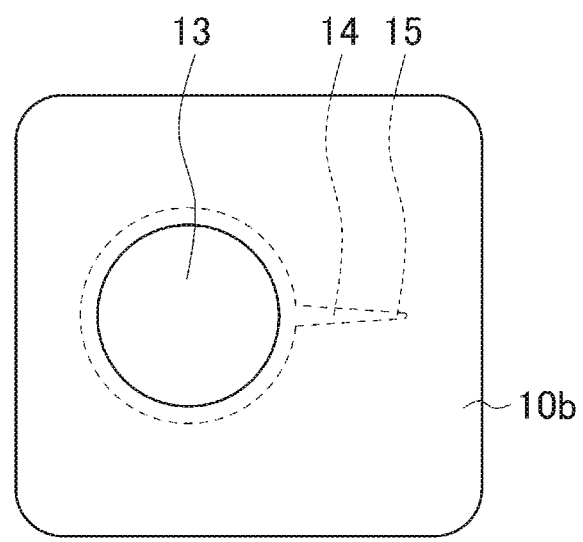
Figure 1C:
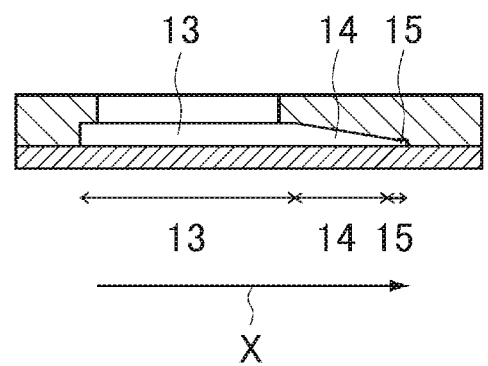

FIGS. 1A, 1B, and 1C provide schematic views of one example of the analysis chip according to the invention. FIG. 1A is a perspective view, FIG. 1B is a top view, and FIG. 1C is a cross-sectional view taken along line I-I of FIG. 1A.

As shown in FIGS. 1A, 1B, and 1C, an analysis chip 1' includes a substrate 10, which is composed of a lower substrate 10a and an upper substrate 10b. The upper substrate 10b is provided with a through-hole and recesses 13, 14, and 15 on the lower surface, which form a reaction section opening, a reaction section 13, a second flow channel 14, and a detection section 15, respectively, as a result of disposing the upper substrate 10b and the lower substrate 10a in layers. The reaction section 13 is communicated with the detection section 15 via the second flow channel 14. In FIG. 1C, the arrow X indicates the direction of the flow of a sample in the analysis chip 1' (longitudinal direction of the analysis chip 1').

The size of the analysis chip 1' is not particularly restricted, and the following conditions can be exemplified.

Reaction Section 13:
Diameter=1 mm to 30 mm (e.g., 8 mm)
Volume of sample to be introduced=1 μL to 1,000 μL (e.g., 50 μL)

Second Flow Channel 14:
Length=10 μm to 5,000 μm (e.g., 2,500 μm)
Width of the end portion on the reaction section 13 side=100 μm to 5,000 μm (e.g., 1,000 μm)
Depth of the end portion on the reaction section 13 side=100 μm to 5,000 μm (e.g., 2,000 μm)
Width of the end portion on the detection section 15 side=10 μm to 1,000 μm (e.g., 150 μm)
Depth of the end portion at the detection section 15 side=10 μm to 1,000 μm (e.g., 150 μm)

Detection Section 15:
  Length=10 µm to 1,000 µm (e.g., 220 µm)
  Width=10 µm to 1,000 µm (e.g., 150 µm)
  Depth=10 µm to 1,000 µm (e.g., 150 µm)
  Volume=0.001 nL to 1,000 nL (e.g., 5 nL)

As shown in FIGS. 1A, 1B, and 1C, the second flow channel 14 has a constricted shape that narrows in a direction from the reaction section 13 toward the detection section 15. Specifically, the second flow channel 14 has a shape in which, as shown in FIG. 1B, the channel tapers inward on both sides from the reaction section 13 toward the detection section 15 when viewed from the upper side of the analysis chip 1' and, as shown in FIG. 1C, the upper surface thereof tapers downward from the reaction section 13 toward the detection section 15 when viewed from the lateral side of the analysis chip 1'.

In the reaction section 13 of the analysis chip 1', the analysis carrier is arranged (not shown). As described above, it is preferable that the analysis carrier is immobilized by the water-soluble material described above.

The analysis of an RNA in a sample using the analysis chip 1' can be performed, for example, as follows. The following embodiment is one example of a case in which the fluorescence label of the fluorescently labeled probe is a pyrene-containing substance and the carrier having the fluorescently labeled probe immobilized thereon is a magnetic carrier.

First, a sample is introduced to the reaction section 13 of the analysis chip 1' via the opening. Then, the analysis carrier (analysis magnetic carrier) in the reaction section 13 is caused to rotate about its axis using a magnet arranged outside the analysis chip 1', thereby bringing the sample into contact with the analysis carrier in the reaction section 13. As a result, the target RNA in the sample and the fluorescently labeled probe in the analysis carrier are bound with each other.

Next, the analysis chip 1' is centrifuged to make the analysis carrier to move from the reaction section 13 to the detection section 15 through the second flow channel 14 by a centrifugal force (C2). Then, the detection section 15 is irradiated with a UV light (e.g., 340 nm) from the upper side of the analysis chip 1', and the fluorescence from pyrene, which is emitted as a result of the binding between the target RNA and the fluorescently labeled probe, is detected at a prescribed wavelength (e.g., 480 nm) using a photodetector. Since the fluorescently labeled probe modified with pyrene emits fluorescence only in a state of being bound with the target RNA, the presence or absence and the amount of the fluorescence from pyrene show a correlation with the presence or absence and the amount of the target RNA. Therefore, by detecting the fluorescence, the target RNA can be analyzed qualitatively or quantitatively.

Figure 2:
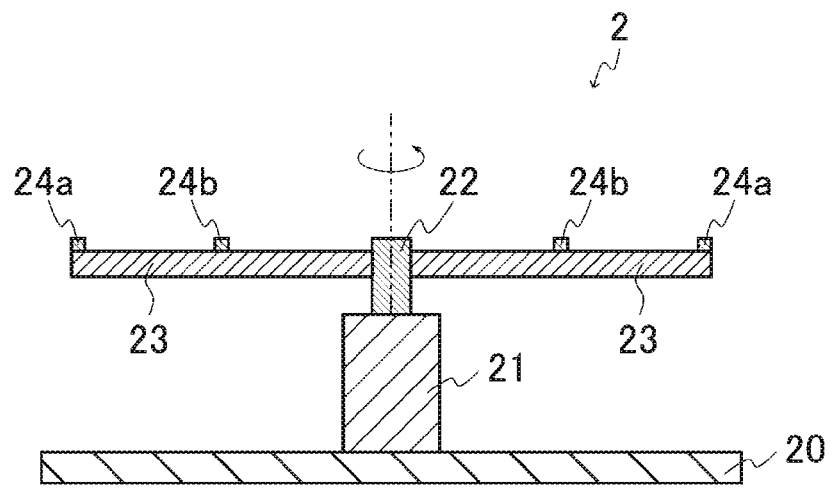
FIG. 2 is a cross-sectional view of one example of a centrifuge.
Figure 3:
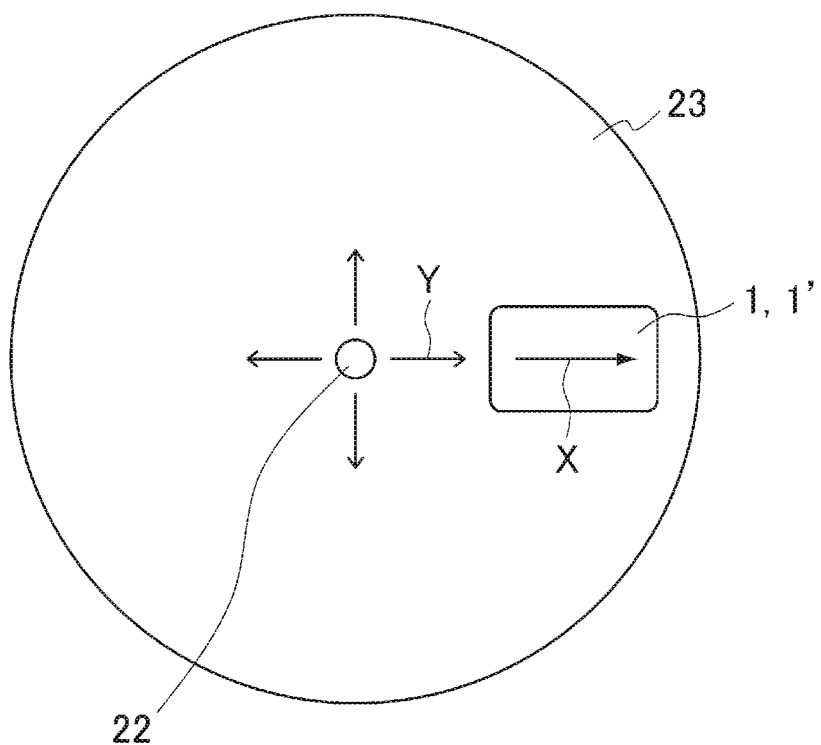
FIG. 3 is a schematic view of one example of a state in which the target analysis chip is placed on a centrifuge.

In the invention, for example, a centrifuge can be used to apply a centrifugal force to the analysis chip as described above. FIGS. 2 and 3 show schematic views of one example of the centrifuge.

FIG. 2 is a cross-sectional view of a centrifuge. A centrifuge 2 includes a substrate 20, a motor 21, a shaft 22, and a stage 23. The stage 23 is provided with fixation parts 24a and 24b, which are used for fixing the analysis chip placed thereon. FIG. 3 is a plan view showing the upper surface of the stage 23 of the centrifuge 2.

The analysis chip can be arranged on the centrifuge 2, for example, as follows. First, the analysis chip 1' is arranged on the stage 23. In this process, the analysis chip 1' is arranged such that its reaction section side is on the side of the shaft 22. Subsequently, the analysis chip 1' is fixed on the stage 23 by the fixation parts 24a and 24b. Then, the motor 21 is driven to rotate the stage 23 about the shaft 22. As a result, a centrifugal force is applied in the direction of the arrow Y from the side of the reaction section of the analysis chip 1' toward the side of the detection section, so that the sample or the analysis carrier can be moved in the analysis chip 1' in the direction of the arrow X.

Fourth Embodiment

The forth embodiment is one example of the analysis method in which the analysis chip of the second embodiment is used and a target RNA as the target is analyzed.

The analysis method of the fourth embodiment is the same as the analysis method of the third embodiment, except that the chip of the second embodiment is used in place of the analysis chip of the first embodiment. Thus, unless otherwise specified, the descriptions of the analysis method of the third embodiment can be applied to the analysis method of the fourth embodiment.

Figure 4A:
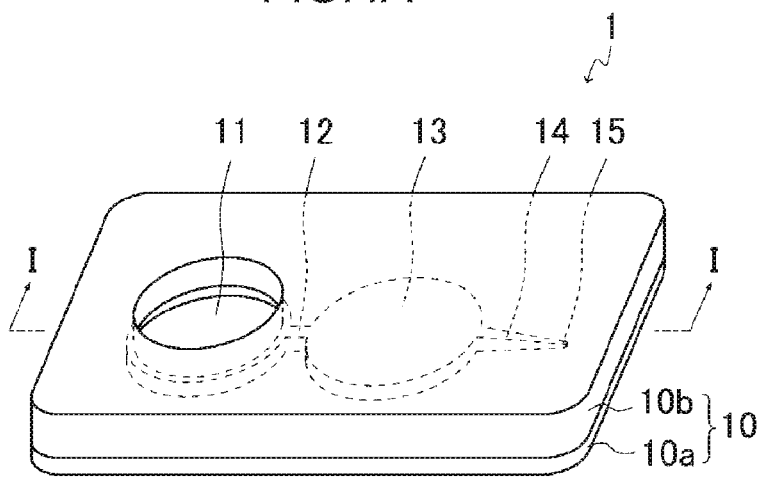
FIGS. 4A, 4B, and 4C are schematic views of another example of the target analysis chip according to the invention.
Figure 4B:
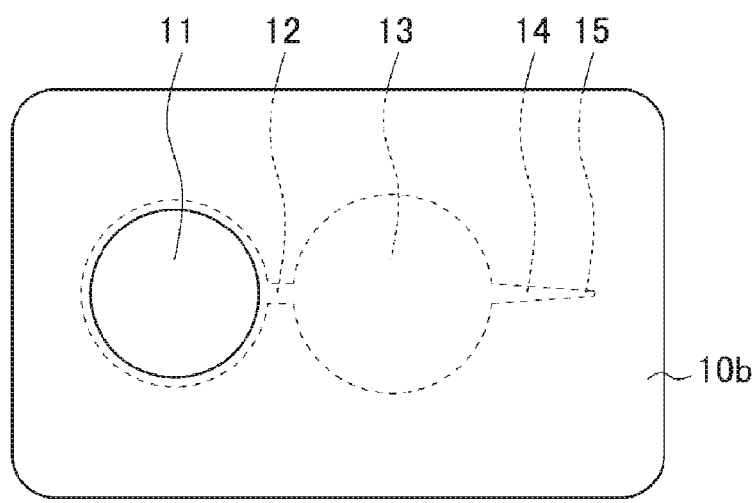
Figure 4C:
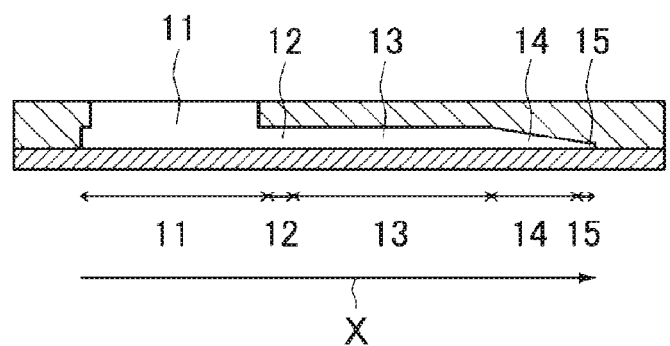

FIGS. 4A, 4B, and 4C provide schematic views showing another example of the analysis chip according to the invention. FIG. 4A is a perspective view, FIG. 4B is a top view, and FIG. 4C is a cross-sectional view taken along line I-I of FIG. 4A.

As shown in FIGS. 4A, 4B, and 4C, an analysis chip 1 includes the substrate 10, which is composed of the lower substrate 10a and the upper substrate 10b. The upper substrate 10b is provided with a through-hole 11 and recesses 12, 13, 14, and 15 on the lower surface, which form a sample introduction section 11, a first flow channel 12, the reaction section 13, the second flow channel 14, and the detection section 15, respectively, as a result of disposing the upper substrate 10b and the lower substrate 10a in layers. The sample introduction section 11 is communicated with the reaction section 13 via the first flow channel 12, and the reaction section 13 is communicated with the detection section 15 via the second flow channel 14. In FIG. 4C, the arrow X indicates the direction of the flow of a sample in the analysis chip 1 (longitudinal direction of the analysis chip 1).

The size of the analysis chip 1 is not particularly restricted, and the following conditions can be exemplified.
Sample Introduction Section 11:
  Diameter=1 mm to 10 mm (e.g., 5 mm)
  Volume of sample to be introduced=1 µL to 1,000 µL (e.g., 50 µL)
Reaction Section 13:
  Diameter=1 mm to 30 mm (e.g., 8 mm)
Second Flow Channel 14:
  Length=10 µm to 5,000 µm (e.g., 2,500 µm)
  Width of the end portion on the reaction section 13 side=100 µm to 5,000 µm (e.g., 1,000 µm)
  Depth of the end portion on the reaction section 13 side=100 µm to 5,000 µm (e.g., 2,000 µm)
  Width of the end portion on the detection section 15 side=10 µm to 1,000 µm (e.g., 150 µm)
  Depth of the end portion on the detection section 15 side=10 µm to 1,000 µm (e.g., 150 µm)
Detection Section 15:
  Length=10 µm to 1,000 µm (e.g., 220 µm)
  Width=10 µm to 1,000 µm (e.g., 150 µm)
  Depth=10 µm to 1,000 µm (e.g., 150 µm)
  Volume=0.001 nL to 1,000 nL (e.g., 5 nL)

As shown in FIGS. 4A, 4B, and 4C, the second flow channel 14 has a constricted shape that narrows in a direction from the reaction section 13 toward the detection section 15. Specifically, the second flow channel 14 has a shape in which, as shown in FIG. 4B, the channel tapers inward on both sides from the reaction section 13 toward the detection section 15 when viewed from the upper side of the analysis chip 1 and, as shown in FIG. 4C, the upper surface tapers downward from the reaction section 13 toward the detection section 15 when viewed from the lateral side of the analysis chip 1.

In the reaction section 13 of the analysis chip 1 analysis carrier is arranged (not shown). It is preferable that the analysis carrier is immobilized by the water-soluble material described above.

The analysis of an RNA in a sample using the analysis chip 1 can be performed, for example, as follows. The following embodiment is one example of a case in which the fluorescence label of the fluorescently labeled probe is a pyrene-containing substance and the carrier having the fluorescently labeled probe immobilized thereon is a magnetic carrier.

First, a sample is introduced to the sample introduction section 11 of the analysis chip 1. Then, the analysis chip 1 is centrifuged to make the sample to move from the sample introduction section 11 to the reaction section 13 through the first flow channel 12 by a centrifugal force (C1). After the completion of the centrifugation, the analysis carrier (analysis magnetic carrier) in the reaction section 13 is caused to rotate about its axis using a magnet arranged outside the analysis chip 1, thereby bringing the sample into contact with the analysis carrier in the reaction section 13. As a result, the target RNA in the sample and the fluorescently labeled probe in the analysis carrier are bound with each other.

Next, the analysis chip 1 is centrifuged to make the analysis carrier to move from the reaction section 13 to the detection section 15 through the second flow channel 14 by a centrifugal force (C2). Then, the detection section 15 is irradiated with a UV light (e.g., 340 nm) from the upper side of the analysis chip 1, and the fluorescence from pyrene, which is emitted as a result of the binding between the target RNA and the fluorescently labeled probe, is detected at a prescribed wavelength (e.g., 480 nm) using a photodetector. Since the fluorescently labeled probe modified with pyrene emits fluorescence only in a state of being bound with the target RNA, the presence or absence and the amount of the fluorescence from pyrene show a correlation with the presence or absence and the amount of the target RNA. Therefore, by detecting the fluorescence, the target RNA can be analyzed qualitatively or quantitatively.

In the invention, for example, a centrifuge can be used to apply a centrifugal force to the analysis chip as described above.

The analysis chip can be arranged on the centrifuge 2, for example, as follows. First, the analysis chip 1 is arranged on the stage 23. In this process, the analysis chip 1 is arranged such that its sample introduction section side is on the side of the shaft 22. Subsequently, the analysis chip 1 is fixed on the stage 23 by the fixation parts 24a and 24b. Then, the motor 21 is driven to rotate the stage 23 about the shaft 22. As a result, a centrifugal force is applied in the direction of the arrow Y from the side of the sample introduction section of the analysis chip 1 toward the side of the detection section, so that the sample or the analysis carrier can be moved in the analysis chip 1 in the direction of the arrow X.

EXAMPLES

Hereinbelow, examples of the invention are described. However, the invention is not limited to the following examples.

Example 1

The analysis chip as shown in FIGS. 4A, 4B, and 4C was prepared, and a miRNA contained in a sample was analyzed.

(1) Production of Flow Channel Structure

The upper substrate 10b of the analysis chip as shown in FIGS. 4A, 4B, and 4C was prepared by the method described below. The size and material of the respective parts of the analysis chip were as follows.

Sample introduction section 11: a circular through-hole of 6 mm in diameter

Reaction section 13: depth=2 mm, diameter=8 mm, a circular shape

First flow channel 12: length=2 mm, width=1 mm, depth=1 mm

Detection section 15: width=0.15 mm, depth=0.15 mm, length=0.3 mm, a rectangular parallelepiped shape Second flow channel 14: length=3.3 mm, width=0.5 mm, and the depth changes via a gradient from 1 mm on the upstream side to 0.15 mm on the downstream side Material: polydimethylsiloxane (PDMS)

First, for producing a flow channel structure having the above-described configuration, an aluminum mold for a flow channel as a casting mold was prepared by cutting work. Then, a PDMS prepolymer solution was poured into the mold for a flow channel and subjected to heat curing in an oven at 70° C. for 1 hour. Thereafter, the cured PDMS molded article was gently peeled off from the mold for a flow channel, thereby obtaining the flow channel structure. The PDMS prepolymer mixed solution was one prepared by mixing a PDMS prepolymer and a curing agent (a base compound and a curing agent of SILPOT; trade name, manufactured by Dow Corning Toray Co., Ltd.) to homogeneity at a weight ratio of 10:1 and subsequently treating the resulting mixed solution under reduced pressure in a desiccator to remove air bubbles generated during the mixing.

(2) Immobilization of Pyrene RNA Probe

As a fluorescently labeled probe, a pyrene-labeled probe (pyrene-RNA probe) was prepared as follows. A polyribonucleotide having a sequence complementary to a miRNA let-7a (AAC AU ACA ACC UAC UA<u>C</u> <u>C</u>UC A (SEQ ID NO:1)) was synthesized. Then, two cytosine residues in this RNA (underlined bases in the sequence) were modified with pyrene, and the base at the 5'-end was modified with psoralen. The resultant was used as a pyrene-RNA probe.

Next, the pyrene-RNA probe was immobilized on beads as follows. As the beads, silica beads of 1 μm in diameter whose surface had been modified with carboxyl groups (trade name: SICASTAR, manufactured by Thermo Fisher Scientific Inc.) were used. The carboxyl groups of the beads were activated by mixing the beads in an aqueous solution containing 1-ethyl-3-(3-dimethylaminopropyl)carbodiimide hydrochloride and hydroxysuccinimide. In the aqueous solution, the amount of the beads was 10 mg, the amount of 1-ethyl-3-(3-dimethylaminopropyl)carbodiimide hydrochloride was 38 mg, and the amount of hydroxysuccinimide was 3 mg. After the activation, in order to remove 1-ethyl-3-(3-dimethylaminopropyl)carbodiimide hydrochloride and hydroxysuccinimide that did not react with the carboxyl groups of the beads, a series of washing operations consisting of centrifugation of the aqueous solution, removal of the supernatant, and addition of distilled water was repeated three times. Then, the pyrene-RNA probe was made to react with the activated carboxyl groups on the beads surface by mixing the pyrene-RNA probe and the beads in a 10 mmol/L phosphate buffer (pH 7.0), whereby the pyrene-RNA probe was immobilized on the beads surface. In the phosphate buffer, the amount of the pyrene-RNA probe was 0.1 nmol. Thereafter, in order to remove the pyrene-RNA probe that was not immobilized on the beads surface, a series of washing operations consisting of centrifugation of the phosphate buffer containing the beads and the pyrene-RNA probe, removal of the supernatant, and subsequent addition of distilled water was repeated three times. In this manner, the beads having the pyrene-RNA probe immobilized thereon were prepared.

(3) Preparation of Reaction Reagent Solution

A reaction reagent solution was prepared by mixing the obtained beads, mannitol, and bovine serum albumin in distilled water at 0.05% w/v, 2% w/v, or 1% w/v.

(4) Immobilization of Reaction Reagent

On the surface of a 0.17 mm-thick borosilicate glass plate, 5 µL of the reaction reagent solution was dropped, and a stainless steel ball of 0.5 mm in diameter was placed on the dropped reaction reagent solution. Then, the glass plate was incubated for 24 hours in an incubator at a temperature of 25° C. and a humidity of 0% to dry the reaction reagent solution and immobilize the stainless steel ball on the glass plate.

(5) Analysis Chip

For the flow channel structure obtained in the above (1), the surface on which the flow channel was formed (the surface to be bonded to the glass plate) was subjected to an oxygen plasma treatment. Then, the treated flow channel structure and the glass plate were bonded together, thereby preparing an analysis chip. The bonding of the flow channel structure and the glass plate was performed such that the reaction section of the flow channel structure was positioned to face the reaction reagent on the glass substrate.

(6) Analysis

A miRNA sample was prepared by mixing 1 pg of let-7a in 0.1 mL of a 10 mmol/L phosphate buffer (pH 7.4). Then, 50 µL of the miRNA sample was added dropwise to the sample introduction section 11 of the analysis chip, and subsequently the analysis chip was fixed on the stage 23 of the centrifuge 2 shown in FIG. 2. The analysis chip was rotated at 1,500 rpm (radius of rotation=50 mm) for 10 seconds to generate a centrifugal force in the direction of the arrow Y as shown in FIG. 3, thereby causing the miRNA sample in the analysis chip made to move from the sample introduction section 11 to the reaction section 13 (in the direction of the arrow X). In the analysis chip, the cross-sectional area of the second flow channel 14 that communicates the reaction section 13 with the detection section 15 is smaller than that of the first flow channel 12, and PDMS used as the material of the analysis chip is hydrophobic (having a contact angle of 110° with respect to distilled water), and therefore, the capillary resistance (resistance force (R)) of the second flow channel 14 is greater than that of the first flow channel 12. As a result, in this process, the miRNA sample is caused to pass through the first flow channel 12, but does not pass through the second flow channel 14 by the above-described centrifugal force. Therefore, the miRNA sample is caused to move from the sample introduction section 11 to the reaction section 13 but does not enter the second flow channel 14, and remains in the reaction section 13.

Next, while irradiating the reaction section 13 of the analysis chip with a LED light having a wavelength of 365 nm, the stainless steel ball in the reaction section 13 was caused to rotate (at 200 rpm) by a magnetic force, whereby the reaction reagent was dissolved by the miRNA sample and mixed with the miRNA. This operation was performed for 10 minutes. As a result of the mixing, let-7a contained in the miRNA sample was attached to the reaction reagent (beads having the pyrene-RNA probe immobilized thereon). Further, by the irradiation with a LED light having a wavelength of 365 nm, psoralen of the pyrene-RNA probe was covalently attached to let-7a. As a result, let-7a contained in the miRNA sample can be efficiently captured on the beads surface of the reaction reagent since the attachment therebetween can be stabilized and their separation can be inhibited.

Next, the analysis chip was rotated at 4,000 rpm (radius of rotation=50 mm) for 60 seconds to cause the beads in the reaction section 13 to move to the detection section 15. The beads have a specific gravity of about 2, which is greater than that of the miRNA sample, and thus accumulated in the detection section 15. Since the total volume of the beads in the reaction reagent is 5 nL, the beads are accumulated within a region that is 0.2 mm to 0.3 mm from the downstream end of the detection section 15 having a 0.15-mm square cross-section.

Thereafter, using a fluorescence microscope, the beads accumulated in the end portion of the detection section 15 of the analysis chip were irradiated with an excitation light having a wavelength of 340 nm, and the fluorescence intensity at a wavelength of 480 nm was measured.

Example 2

The analysis chip as shown in FIGS. 1A, 1B, and 1C was prepared, and a miRNA contained in a sample was analyzed.

(1) Analysis Chip

The upper substrate 10b of the analysis chip shown in FIGS. 1A, 1B, and 1C was prepared by the method described below. The analysis chip was prepared in the same manner as items (1) to (5) in Example 1, except that the size and material of the respective parts were changed as follows.

Reaction section 13: depth=2 mm, diameter=8 mm, a circular shape, with a circular through-hole of 6 mm in diameter Detection section 15: width=0.15 mm, depth=0.15 mm, length=0.3 mm, a rectangular parallelepiped shape Second flow channel 14: length=3.3 mm, width=0.5 mm, and the depth changes via a gradient from 1 mm on the upstream side to 0.15 mm on the downstream side Material: polydimethylsiloxane (PDMS)

(2) Analysis

Each of miRNA samples was prepared by mixing let-7a in a 10 mmol/L phosphate buffer (pH 7.4) at a prescribed concentration (0 mol/L, 50 fmol/L, 200 fmol/L, 2 pmol/L, 20 pmol/L, or 200 pmol/L). Then, 50 µL of the each miRNA sample was added dropwise to the reaction section 13 of the analysis chip, and subsequently the analysis chip was fixed on the stage 23 of the centrifuge 2 shown in FIG. 2.

While irradiating the reaction section 13 of the analysis chip with a LED light having a wavelength of 365 nm, the stainless steel ball in the reaction section 13 was caused to rotate (at 200 rpm) by a magnetic force, whereby the reaction reagent was dissolved by the miRNA sample and mixed with the miRNA sample. This operation was performed for 10 minutes. As a result of the mixing, let-7a contained in the miRNA sample was attached to the reaction reagent (beads having the pyrene-RNA probe immobilized thereon). Further, by the irradiation with a LED light having a wavelength of 365 nm, psoralen of the pyrene-RNA probe was covalently attached to let-7a. As a result, let-7a contained in the miRNA sample can be efficiently captured on the beads surface of the reaction reagent since the attachment therebetween can be stabilized and their separation can be inhibited.

Next, the analysis chip was rotated at 4,000 rpm (radius of rotation=50 mm) for 60 seconds to cause the beads in the reaction section 13 to move to the detection section 15. The beads have a specific gravity of about 2, which is greater than that of the miRNA sample, and thus accumulated in the detection section 15. Since the total volume of the beads in the reaction reagent is 5 nL, the beads are accumulated within a region that is 0.2 mm to 0.3 mm from the downstream end of the detection section 15 having a 0.15-mm square cross-section.

Thereafter, using a fluorescence microscope, the beads accumulated in the end portion of the detection section 15 of the analysis chip were irradiated with an excitation light having a wavelength of 340 nm, and the average fluorescence intensity at a wavelength of 480 nm was measured.

Figure 5A:
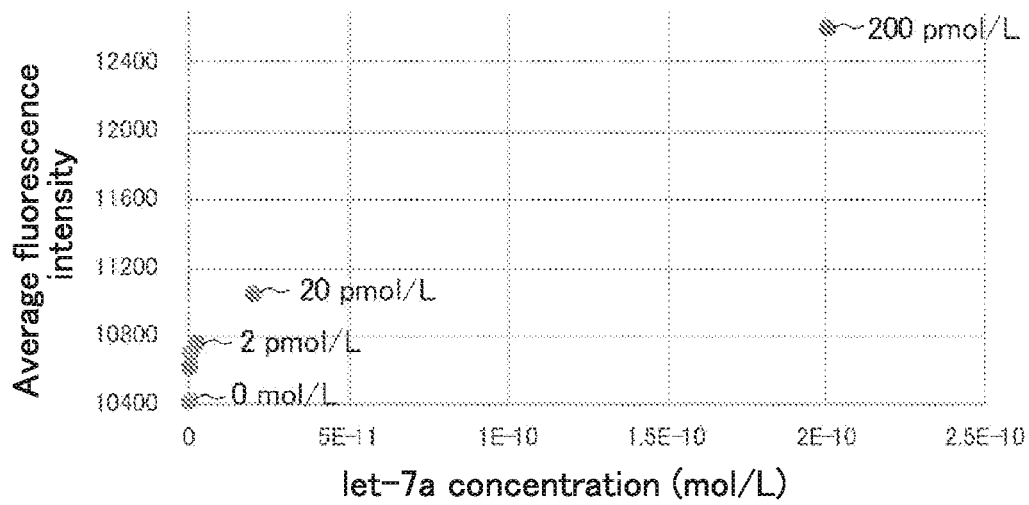
FIGS. 5A and 5B are graphs showing the average fluorescence intensity measured in Example 2.
Figure 5B:
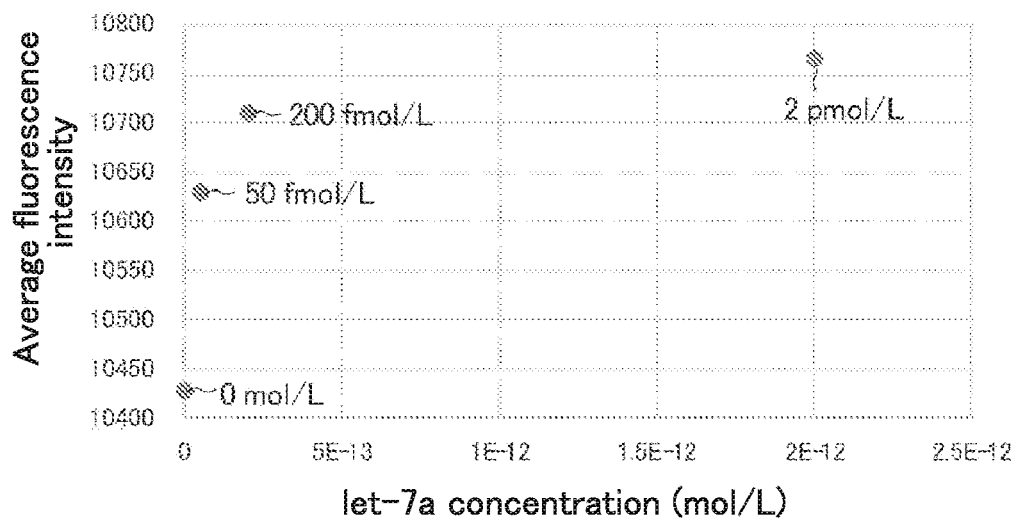

The results are shown in FIGS. 5A and 5B. FIGS. 5A and 5B provide graphs showing the average fluorescence intensity. FIG. 5A shows the results of all miRNA samples, and FIG. 5B shows the results of the 0 to 2 pmol/L miRNA samples. Further, in each of FIGS. 5A and 5B, the horizontal axis indicates the miRNA concentration, and the longitudinal axis indicates the average fluorescence intensity. As shown in FIGS. 5A and 5B, the average fluorescence intensity increased in a miRNA concentration-dependent manner. Moreover, it was found that, by using the analysis chip, a miRNA can be detected even at an extremely low concentration of 50 fmol/L without using PCR. From these results, it was found that, according to the analysis chip and analysis method of the invention, sufficient sensitivity and accuracy can be achieved in the analysis of a target contained in a sample.

Example 3

Using analysis chips having different depths of detection section and beads having different diameters, it was conformed that the beads could be recovered in the detection section.

(1) Analysis Chip

Analysis chips were each prepared in the same manner as item (1) in Example 2, except that the depth of the detection section 15 was changed to 40 μm, 70 μm, 100 μm, or 150 μm and that rhodamine fluorescently-labeled silica beads having a diameter of 300 nm, 800 nm, 5 μm, or 10 μm (manufactured by micromod Partikeltechnologie GmbH) were used in place of the beads having the pyrene-RNA probe immobilized thereon.

(2) Analysis

50 μL of the phosphate buffer was added dropwise to the reaction section 13 of each analysis chip, and subsequently the analysis chip was fixed on the stage 23 of the centrifuge 2 as shown in FIG. 2.

The stainless steel ball in the reaction section 13 of the analysis chip was caused to rotate (at 200 rpm) by a magnetic force, whereby the reaction reagent was dissolved by the miRNA sample. This operation was performed for 10 minutes. Next, the analysis chip was rotated at 4,000 rpm (radius of rotation=50 mm) for 60 seconds to cause the beads in the reaction section 13 to move to the detection section 15.

Thereafter, using a fluorescence microscope, the beads accumulated in the end portion of the detection section 15 of the analysis chip were irradiated with an excitation light having a wavelength of from 510 nm to 560 nm, and the average fluorescence intensity and the absorbance were measured at a wavelength of 490 nm or longer.

Figure 6A:
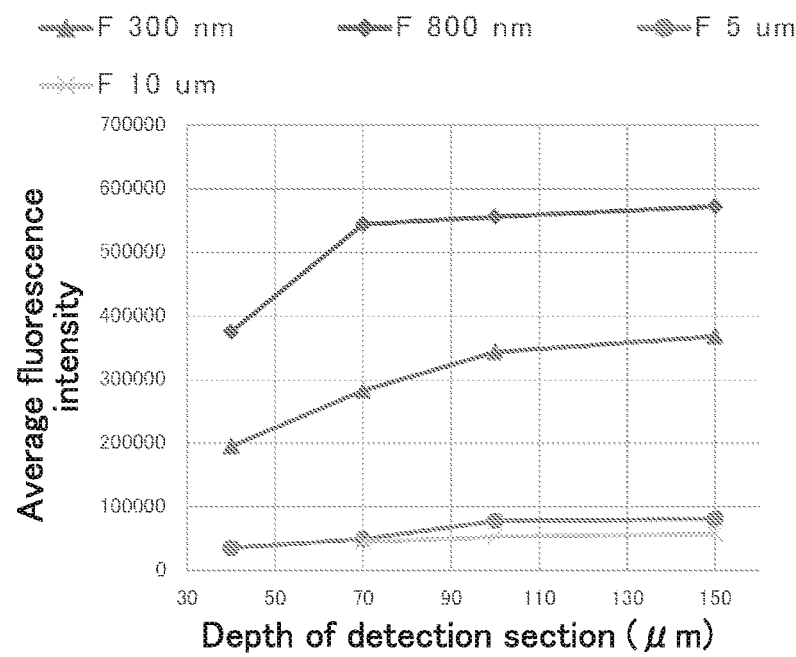
FIG. 6A is a graph showing the average fluorescence intensity measured in Example 3.
Figure 6B:
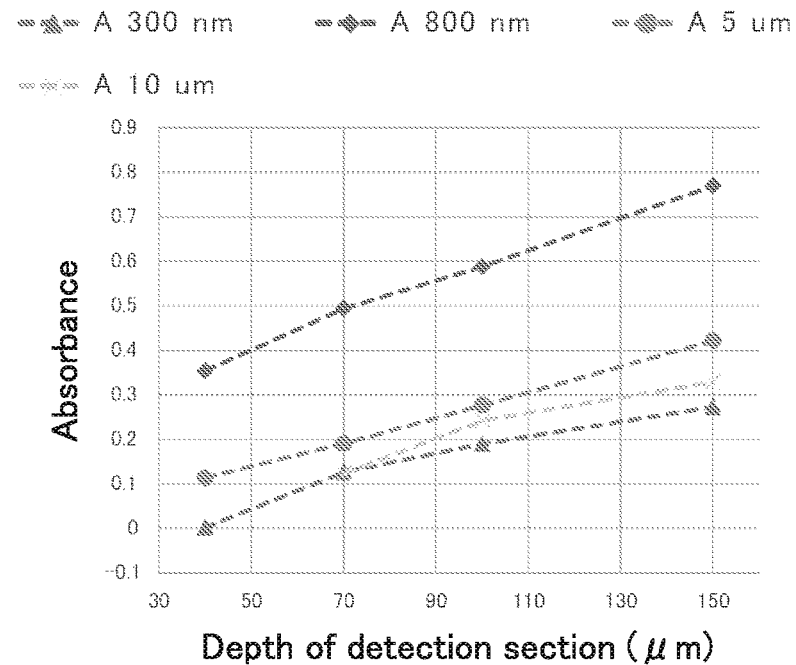
FIG. 6B is a graph showing the absorbance measured in Example 3.

The results are shown in FIGS. 6A and 6B. FIGS. 6A and 6B provide graphs showing the average fluorescence intensity or the absorbance. FIG. 6A shows the measurement result of the average fluorescence intensity, and FIG. 6B shows the measurement result of the absorbance. In FIGS. 6A and 6B, triangles represent the result using the 300-nm beads, rhomboids represent the result using 800-nm beads, circles represent the result using 5-μm beads, and crosses represent the result using 10-μm beads. In FIG. 6A, the horizontal axis indicates the depth of the detection section 15 and the longitudinal axis indicates the average fluorescence intensity. In FIG. 6B, the horizontal axis indicates the depth of the detection section 15 and the longitudinal axis indicates the absorbance. As shown in FIG. 6A, in all of the cases using the beads having different diameters, the average fluorescence intensity increased in conjunction with increased depth of the detection section 15. In addition, it was found that, among these beads, the 300-nm beads exhibited a high and constant increase rate of average fluorescence intensity in conjunction with increased depth of the detection section 15 and can thus be particularly preferably used as the above-described carrier. Moreover, as shown in FIG. 6B, in all of the cases using the beads having different diameters, the absorbance increased in conjunction with increased depth of the detection section 15. Furthermore, the 300-nm, 5-μm and 10-μm beads all exhibited a reduced absorbance at any depth of the detection section 15 and, therefore, it was found that these beads can reduce detection failure when, for example, detecting a label by an optical method.

Example 4

Using a surfactant at different concentrations and analysis chips in which the side surface of the second flow channel 14 was a curved surface that tapers from the reaction section 13 toward the detection section 15 and the radius of curvature of the curved surface was different, it was conformed that the beads was recovered in the detection section.

(1) Analysis Chip

Figure 7A:
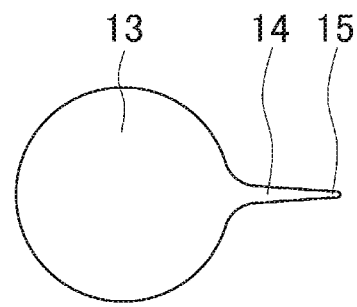
FIGS. 7A, 7B, and 7C are end views of the inside of each of the analysis chips used in Example 4.
Figure 7B:
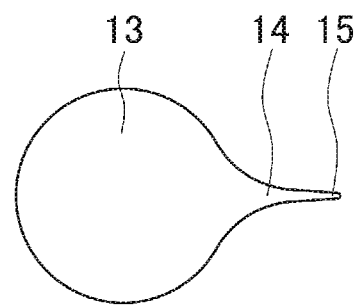
Figure 7C:
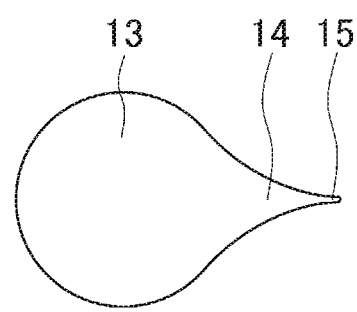

As shown in FIGS. 7A, 7B, and 7C, analysis chips were each prepared in the same manner as item (1) in Example 2, except that the side surface of the second flow channel 14 was a curved surface tapering from the reaction section 13 toward the detection section 15; that the depth of the detection section 15 was set at 100 μm; and that 300-μm or 5-μm rhodamine-labeled silica beads were used in place of the beads having the pyrene-RNA probe immobilized thereon. Here, in the analysis chips of FIGS. 7A, 7B, and 7C, the radius of curvature (R) of each tapering curved surface was 1.5 mm, 3 mm, and 4.5 mm, respectively.

(2) Analysis

50 μL of a 10 mmol/L phosphate buffer (pH 7.4) containing 0.5% TWEEN 20 (registered trademark) or TRITON (trademark) X-100 was added dropwise to the reaction section 13 of each of the analysis chips, and the beads were made to accumulate in the detection section 15 in the same manner as item (2) in Example 3. Then, using a fluorescence microscope, the beads accumulated in the end portion of the detection section 15 of the analysis chip were irradiated with an excitation light having a wavelength of from 510 nm to 560 nm, and the sum of the fluorescence intensity (total fluorescence intensity) measured at a wavelength of 490 nm or longer for the part where the beads were accumulated was determined. Further, the total fluorescence intensity was determined in the same manner in advance of the addition of the beads, and the total fluorescence intensity was corrected by subtracting the total fluorescence intensity determined before the addition of the beads from the total fluorescence intensity determined after the addition of the beads (corrected total fluorescence intensity).

Figure 8A:
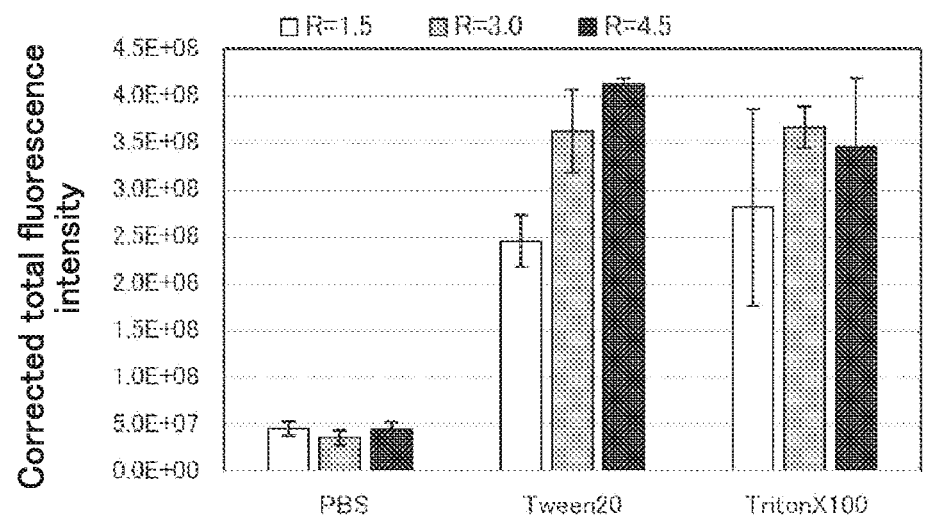
FIGS. 8A and 8B are graphs showing the corrected total fluorescence intensity determined in Example 4.
Figure 8B:
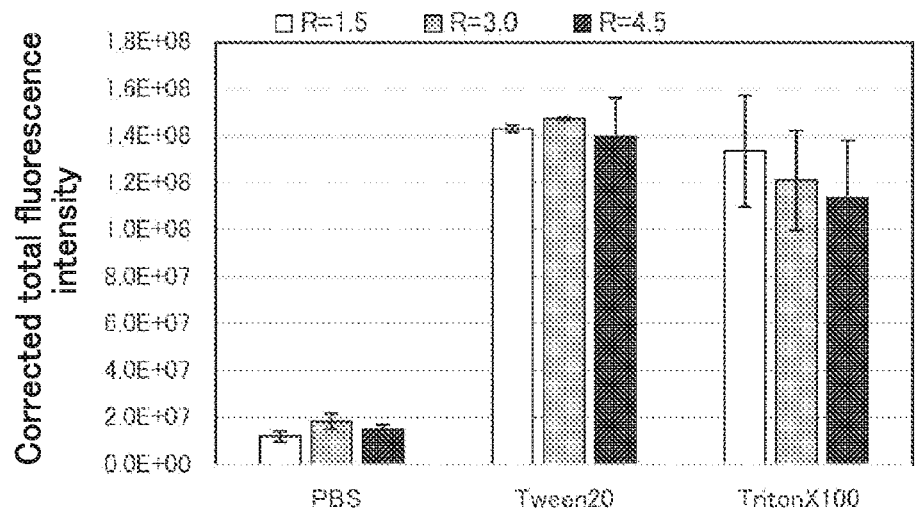

The results are shown in FIGS. 8A and 8B. FIGS. 8A and 8B provide graphs showing the corrected total fluorescence intensity. FIG. 8A shows the result using 5-μm beads, and FIG. 8B shows the result using 300-nm beads. In each of FIGS. 8A and 8B, the horizontal axis indicates the type of the surfactant, and the longitudinal axis indicates the corrected total fluorescence intensity. As shown in FIGS. 8A and 8B, it was found that, in cases in which the side surface of the second flow channel 14 was a curved surface having any radius of curvature, the corrected total fluorescence intensity is high and the beads can be efficiently recovered. In addition, as shown in FIGS. 8A and 8B, the corrected total fluorescence intensity was significantly increased in a case in which a surfactant was included compared to the case in which no surfactant was included. That is, it was found that the beads can be efficiently recovered by using a surfactant in the reagent.

applied to the target analysis chip in a very small amount. Therefore, the invention is considered to be useful, for example, in the medical field where targets such as micro-RNAs are analyzed.

DESCRIPTION OF REFERENCE NUMERALS

1, 1': Analysis chip
2: Centrifuge
10a: Lower substrate
10b: Upper substrate
10, 20: Substrate
11: Sample introduction section
12: First flow channel
13: Reaction section
14: Second flow channel
15: Detection section
21: Motor
22: Shaft
23: Stage
24a, 24b: fixation part

SEQUENCE LISTING

```
<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: probe

<400> SEQUENCE: 1
aacauacaac cuacuaccuc a                                              21
```

In the above, the invention was described referring to embodiments; however, the invention is not restricted to the above-described embodiments. In the constitution and details of the invention, a variety of modifications that can be understood by those of ordinary skill in the art can be made within the scope of the invention.

This application claims priority from Japanese Patent Application No. 2015-010639 filed on Jan. 22, 2015, the disclosure of which is hereby incorporated by reference in its entirety.

INDUSTRIAL APPLICABILITY

According to the invention, a target contained in a sample can be directly analyzed without using PCR. Further, in the invention in which the carrier having a labeled probe immobilized thereon is used, the flow channel includes the hydrophobic inner wall as the movement controller, and therefore the movement of the carrier from the reaction section to the detection section can be controlled. Further, by applying a centrifugal force (C2), that is larger than a resistance force (R) caused by the hydrophobicity of the inner wall of the flow channel, to a conjugate of the target and the labeled probe, for example, the conjugate can be recovered in the detection section in a highly concentrated state. Accordingly, in the analysis of a target contained in a sample, sufficient sensitivity and accuracy can be realized, and, for example, the analysis can be performed even when the sample is

The invention claimed is:

1. A target analysis chip, comprising a substrate, the substrate comprising a reaction section at which a sample containing a target is made to react with a reagent, a detection section at which label detection is performed, and a flow channel that communicates the reaction section with the detection section, wherein:

the reagent comprises a carrier;

the carrier comprises a labeled probe immobilized thereon, the labeled probe being configured to bind to the target, and the carrier having a specific gravity of greater than 1 and being configured to form a conjugate with the target;

the flow channel comprises a movement controller configured to control movement of the carrier from the reaction section to the detection section;

the movement controller comprises a hydrophobic inner wall in the flow channel; and due to the movement controller, the conjugate is made to move to the detection section through the flow channel when a centrifugal force (C2), that is larger than a resistance force (R) caused by the hydrophobicity of the flow channel, is applied.

2. The target analysis chip according to claim 1, wherein the flow channel has a structure that narrows in a direction from the reaction section toward the detection section.

3. The target analysis chip according to claim 1, wherein the detection section has a height of from 1 μm to 500.

4. The target analysis chip according to claim 1, wherein a volume of an internal space of the detection section is smaller than a volume of an internal space of the reaction section.

5. The target analysis chip according to claim 1, wherein the carrier is a bead.

6. The target analysis chip according to claim 5, wherein the bead has a diameter of from 100 nm to 4 μm.

7. The target analysis chip according to claim 1, wherein the carrier is made of silica.

8. The target analysis chip according to claim 1, wherein a side surface of the flow channel is a curved surface that tapers from the reaction section toward the detection section.

9. The target analysis chip according to claim 1, wherein a label of the labeled probe is a substance that exhibits a signal change upon binding of the labeled probe to the target.

10. The target analysis chip according to claim 9, wherein the label is a substance containing pyrene.

11. The tact analysis chip according to claim 10, wherein the labeled probe is further modified with psoralen.

12. The target analysis chip according to claim 1, wherein the target is a microRNA.

13. The target analysis chip according to claim 1, wherein the amount of the labeled probe is from 1 zmol to 1 nmol.

14. The target analysis chip according to claim 1, wherein the reaction section also serves as a sample introduction section to which the sample is introduced.

15. The target analysis chip according to claim 1, wherein:
the substrate further comprises a sample introduction section to which the sample is introduced, and a flow channel that communicates the sample introduction section with the reaction section; and
the sample introduced to the sample introduction section is made to move to the reaction section by a centrifugal force (C1) that is smaller than the centrifugal force (C2).

16. The target analysis chip according to claim 15, wherein the flow channel that communicates the sample introduction section with the reaction section further comprises a filter.

17. A target analysis method using the target analysis chip according to claim 1, the target analysis method comprising:
introducing the sample and the reagent to the reaction section;
bringing the sample into contact with the carrier comprising a labeled probe immobilized thereon in the reaction section, thereby causing the target contained in the sample and the labeled probe to undergo a binding reaction and form a conjugate of the target and the labeled probe;
causing the conjugate in the reaction section to move to the detection section by a centrifugal force (C2) that is larger than a resistance force (R) caused by the hydrophobicity of the inner wall of the flow channel; and
analyzing the target contained in the sample in the detection section by detecting the label of the labeled probe bound with the target.

18. The target analysis method according to claim 17, comprising stirring a mixture containing the sample and the carrier in the reaction section.

19. The target analysis method according to claim 17, wherein:
a label of the labeled probe is a substance that exhibits a signal change upon binding of the labeled probe to the target; and
the signal change of the label is detected in the detection section.

20. The target analysis method according to claim 19, wherein:
the label is a substance containing pyrene; and
a fluorescence signal having a wavelength of from 450 nm to 510 nm is detected by irradiating the detection section with a UV light.

* * * * *